US006342517B1

(12) United States Patent
Esch et al.

(10) Patent No.: US 6,342,517 B1
(45) Date of Patent: *Jan. 29, 2002

(54) POTASSIUM CHANNEL ACTIVATORS AND THEIR USE

(75) Inventors: Peter Esch, Grasse (FR); Franz Rovenszky, Linz (AT); Robertson Towart, Stoke Poges (GB); Thomas Christoph, Aachen (DE); Michael Hartmann, Linz (AT); George Terence Evelyn Kealey, Cambridge (GB)

(73) Assignee: Cambridge Bioclinical Limited, Rutland (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/454,029

(22) Filed: Dec. 3, 1999

(30) Foreign Application Priority Data

Dec. 4, 1998 (GB) ............................................... 9826830
Apr. 28, 1999 (GB) ............................................... 9909792

(51) Int. Cl.[7] ...................... A61K 31/40; A61K 31/385; C07D 405/00; C07D 339/02
(52) U.S. Cl. ...................... 514/422; 514/440; 514/436; 548/526; 549/39; 549/22
(58) Field of Search .......................... 548/526; 514/422, 514/440, 436; 549/39, 22

(56) References Cited

U.S. PATENT DOCUMENTS

| | | |
|---|---|---|
| 5,030,736 A | 7/1991 | Press et al. |
| 5,077,307 A | 12/1991 | Binder et al. |
| 5,284,857 A | 2/1994 | Press et al. |
| 5,430,048 A | 7/1995 | Gadwood |

FOREIGN PATENT DOCUMENTS

| | | |
|---|---|---|
| EP | 0350805 | 7/1989 |
| EP | 0360621 | 9/1989 |
| EP | 0405298 | 6/1990 |
| EP | 0747374 | 6/1996 |
| WO | 9202225 | 2/1992 |
| WO | 9209259 | 6/1992 |
| WO | 9413272 | 6/1994 |
| WO | 9413292 | 6/1994 |
| WO | 9637490 | 11/1996 |
| WO | 9714036 | 4/1997 |

OTHER PUBLICATIONS

J.J. McNally et al., J. Heterocyclic Chem. 29:247–251 (1992).
P.J. Sanfilippo et al., J. Med. Chem. 35:23 4425–4433 (1992).
B.P. Damiano et al., Cardiovasc. Drug. Review. 12:1 16–31 (1994).
J.B. Press et al., Bioorganic & Medicinal Chemistry 1:6 423–435(1993).
P.J. Sanfilippo et al., Bioorganic Medicinal Chemistry 3:6 1385–1388 (1993).
B. P. Damiano, et al., J. of Cardiovascular Pharmacology. 23:300–310 (1994).
L.B. Katz, et al. J. of Pharmacology & Experimental Therapeutics 267:648–565 (1993).
H.I. Jacoby, et al. Life Sciences 52: PL233–PL238 (1993).
B.P. Damiano, et al. J. Cardiovascular Pharmacology 22:143–152 91993).
R.C. Gadwood et al. Bioorganic & Medicinal Chemistry Letters 5:18 2101–2104 (1995).
R.C. Gadwood et al. J. Med. Chem. 36:1480–1487 (1993).

Primary Examiner—Deborah C. Lambkin
(74) Attorney, Agent, or Firm—Dann Dorfman Herrell and Skillman, P.C.

(57) ABSTRACT

Novel thienopyran compounds are disclosed, useful as antihypertensive agents and for asthma treatment. One group of the compounds has a heterocyclic ring spiro-connected at the 7-position of the thienopyran ring structure. Use of thienopyran compounds in hair growth modulation is described.

25 Claims, 5 Drawing Sheets

POTASSIUM CHANNEL ACTIVATORS AND THEIR USE

TECHNICAL FIELD

This invention relates to potassium channel activators in the form of thienopyran compounds, preparations and compositions containing them, and their use in mammalian hair growth modulation.

BACKGROUND OF THE INVENTION

Potassium channels (K$^+$ channels) are important cell function regulatory sites. There appears to be a diversity of such channels. Interest in them as sites of therapeutic intervention has increased in recent years (Cook, N. S., Potassium Channels: structure, classification, function and therapeutic potential, Ellis Horwood Ltd., 1990).

Compounds which act as potassium channel activators (potassium channel openers) are known. Research in the area was stimulated by the discovery of cromakalim (described in EP-A-76075), which has a benzopyran-based structure, but the molecular details which cause the activity are not yet elucidated.

U.S. Pat. No. 5,077,307 discloses certain potassium channel activators having a thienopyran ring structure. Specifically, the following two compounds are disclosed:

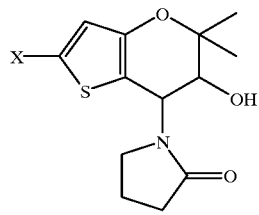

where X is —CN and —CONH$_2$. The hydroxy and oxopyrrolidinyl groups at the 6,7 positions have a trans orientation. The first of these (with X=CN) is disclosed in U.S. Pat. No. 5,077,307 in its racemic form and as each of its enantiomers. The racemic form is referred to below as compound 11901, and the (−)-enantiomer as compound 11903.

Other substituted thienopyrans useful as anti-hypertensive agents and for other purposes are disclosed in U.S. Pat No. 5,284,857.

SUMMARY OF THE INVENTION

The object of the invention in to provide new and useful compounds which have potassium channel activating. activity.

According to the invention in a first aspect there is provided a thienopyran compound having the formula I, II or III

I:

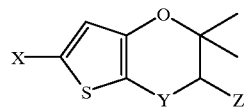

II:

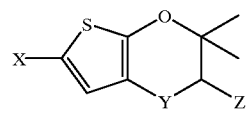

III:

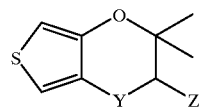

wherein

X is H or an electron-withdrawing group,

Y is an alicyclic or heterocyclic ring spiro-connected to the thienopyran ring at the position indicated by Y, the ring Y being saturated or mono-unsaturated and being substituted or unsubstituted, Z is selected from hydrogen, hydroxy and alkoxy.

Preferably, X is H or an electron-withdrawing group selected from NO$_2$, CN, halogen, halogenated alkyl, alkanoyl (C$_{1-4}$), halogenated alkanoyl (C$_{1-4}$) benzoyl, acylamino (C$_{2-4}$), alkoxycarbonyl (C$_{1-4}$), CHO, COOH, COOR where R is C$_{1-4}$, CH=NOH, CONH$_2$ CON(R')$_2$ or NHCOR' where R' is alkyl (C$_{1-4}$), alkoxy (C$_{1-4}$) or phenyl, oxophosphorus and oxosulphur groups and

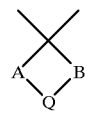

More preferably, X is selected from —CN, halogenated alkyl (preferably of 1–4 C atoms), oxophosphorus or oxosulphur groups (preferably —SO$_2$R$^1$ or PO(OR$^2$), where R$^1$ is substituted or unsubstituted phenyl, pyridyl or thienyl and each R$^2$ is H or alkyl of 1–4 C atoms), oxocarbon groups (e.g. —CHO, —CONR$^3$$_2$, —COOR$^3$, wherein each R$^3$ is H or alkyl of 1–4 C atoms) and —CH=NOH, Ring Y is preferably

wherein Q is selected from saturated and mono-unsaturated carbon chains of 2–4 carbon atoms, and A and B fulfil one of the following; (a) both being carbon atoms, (b) one being S, SO or SO$_2$, and the other a carbon atom, (c) each being S, SO or SO2, (d) one being NR" where R" is hydrogen or alkyl and the other being a carbon atom, (e) each being NR" where R" is hydrogen or alkyl; and each carbon atom of the ring Y is unsubstituted or substituted by one of alkyl, halogen or hydroxy or is a member of a carbonyl group or an epoxy ring.

More preferably Y is of the formula

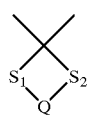

wherein $S_1$ is >S, >SO or $SO_2$ and $S_2$ is part of a carbon chain with Q or is >S, >SO or >$SO_2$, and Q is a saturated or unsaturated (preferably mono-unsaturated) carbon chain of 2–4 C atoms, each carbon atom of the heterocyclic ring being unsubstituted or substituted by alkyl (preferably of 1–4 C atoms), halogen or hydroxy, or is a member of a carbonyl group or an epoxy ring, and Z is hydrogen, hydroxy or alkoxy (preferably of 1–4 C atoms).

Preferably X is —CN, and preferably Z is H.

Preferably Y is selected from the following:

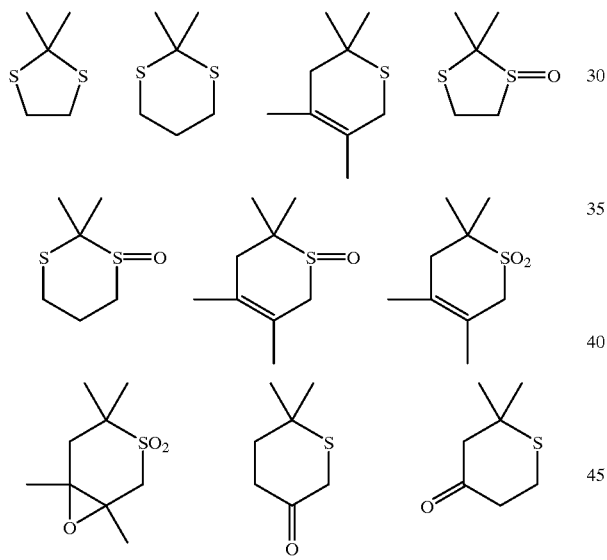

In a second aspect, the invention provides thienopyran compound having the formula I, II or III

I:

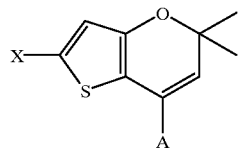

II:

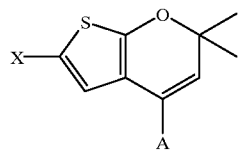

-continued

III:

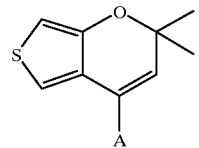

wherein

X is H or an electron-withdrawing group selected from —CN, halogenated alkyl (preferably of 1–4 C atoms), oxophosphorus or oxosulphur groups (preferably —$SO_2R^1$ or $PO(OR^2)_n$ where $R^1$ is substituted or unsubstituted phenyl, pyridyl or thienyl and each $R^2$ is H or alkyl of 1–4 C atoms), oxocarbon groups (e.g. —CHO, —$CONR^3_2$, —$COOR^3$, wherein each $R^3$ is H or alkyl of 1–4 C atoms), —CH=NOH and

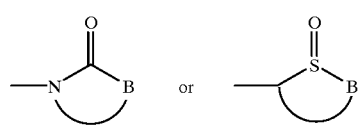

and

A is

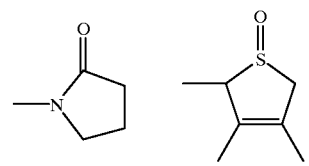

wherein B is a saturated or unsaturated carbon chain of 2–4 C atoms of which each carbon atom is unsubstituted or substituted by alkyl (preferably of 1–4 C atoms), halogen or hydroxy, or is a member of an epoxy ring.

Preferably X is —CN, and preferably A is selected from the following:

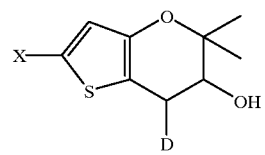

In a third aspect, the invention provides a thienopyran compound having the formula I, II or III

I:

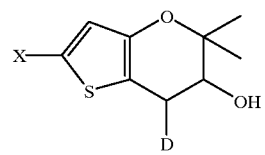

-continued

II:

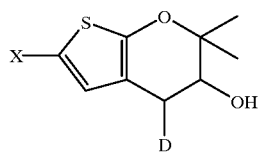

III:

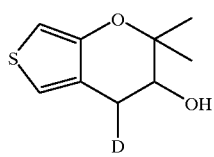

wherein
X is selected from oxophosphorus and oxosulphur groups (preferably —$SO_2R^1$ or $PO(OR^2)_n$ where $R^1$ is substituted or unsubstituted phenyl, pyridyl or thienyl and each $R^2$ is H or alkyl of 1–4 C atoms), and
D is

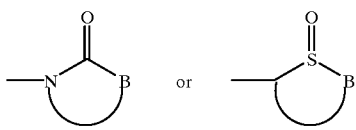

wherein B is a saturated or unsaturated carbon chain of 2–4 C atoms of which each carbon atom is unsubstituted or substituted by alkyl (preferably of 1–4 C atoms), halogen or hydroxy, or is a member of an epoxy ring.

Preferably X is —$SO_2(C_6H_5)$, and preferably D is

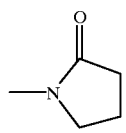

In all three of the above aspects of the invention, the preferred compounds are those having the formula I.

The invention also provides a pharmaceutical preparation comprising a thienopyran compound of the first three aspects above.

Further the invention provides a composition for administration to a human or other mammal, comprising as active ingredient a thienopyran compound of the first three aspects above, particularly a composition effective for hair growth modulation in a human or other mammal.

The results in the K⁺-stimulated isolated rat aorta test given below indicate that the compounds of the invention are potentially useful as anti-hypertensive agents to reduce blood pressure in mammals and also to reduce the immunological response associated with asthma.

As discussed below, it has been found that thienopyran compounds herein described have indications for activity for modulation of mammalian hair growth. Accordingly in another aspect the present invention consists in use of certain thienopyran compounds for hair growth modulation, including known compounds proposed for other purposes as described above. Particularly the invention provides cosmetic hair growth modulation, but hair growth modulation for non-cosmetic purposes is not excluded. In this aspect the invention provides a method of modulation of hair growth in a human or other mammal, comprising topical application of a thienopyran compound (including partially saturated thienopyran compounds, e.g. dihydro thienopyrans) which has activity of hair growth modulation in an amount effective to provide hair growth modulation.

More specifically in this aspect the invention provides a method of modulation of hair growth in a human or other mammal, comprising topical application of an effective amount of at least one thienopyran compound having the formula I, II or III

I:

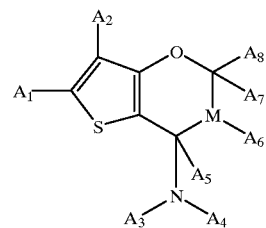

II:

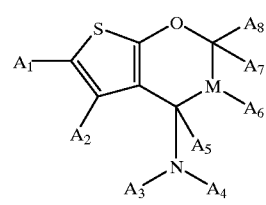

III:

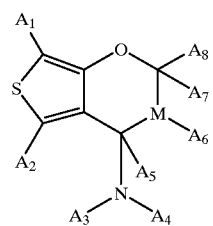

and $A_1$ and $A_2$ are selected from hydrogen, nitro, cyano, trifluoromethyl, halogen, lower alkyl ($C_{1-4}$), alkanoyl ($C_{2-4}$), substituted alkyl ($C_{1-4}$) and substituted alkanoyl ($C_{2-4}$), wherein the substituent is halogen; benzoyl, substituted benzoyl, wherein the substituent is selected from bromo, chloro, iodo, alkyl ($C_{1-4}$), alkoxy ($C_{1-4}$), acyl ($C_2^-$), nitro, cyano and trifluoromethyl; acylamino ($C_{2-4}$), alkoxy carbonyl ($C_{1-4}$), CHO, COOH, CH=NOH, $CONH_2$, $CON(R)_2$ and NHCOR wherein R is alkyl ($C_{1-4}$), alkoxy ($C_{1-4}$), phenyl or substituted phenyl wherein the substituent is selected bromo, chloro, iodo, lower alkyl, lower alkoxy, nitro, cyano, trifluoromethyl and acyl ($C_{2-4}$); oxophosphorus and oxosulphur groups; and

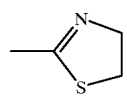

$A_3$ and $A_4$ are selected from hydrogen, hydroxy, alkanoyl ($C_{2-5}$), alkyl ($C_{1-4}$), cycloalkyl ($C_{3-6}$), cycloalkyl carbonyl ($C_{3-6}$), pyridyl carbonyl, benzoyl, substituted benzoyl wherein the substituent is selected from bromo, chloro, iodo, alkyl ($C_{1-4}$), alkoxy ($C_{1-4}$), acyl ($C_{2-4}$), nitro, cyano and trifluoromethyl; or $A_3A_4N$ together are a heterocyclic ring selected from a pyrrole, pyrrolidine or piperidine ring, a ($C_{3-9}$) lactam selected from the group consisting of isoindolone, pyrrolidinone, piperidinone, pyridinone, pyrazinone, and glycine anhydride, or substituted ($C_{3-9}$) lactam; $A_5$ is hydrogen or together with $A_6$ forms a double bond; M is CH or taken together with A, is carbonyl; $A_6$ is hydrogen, hydroxy, alkoxy ($C_{1-6}$), alkanoyloxy ($C_{2-7}$), benzoyloxy, substituted benzoyloxy; and $A_7$ and $A_8$ are hydrogen or alkyl ($C_{1-4}$) or together form a ring having 5–8 carbon atoms; and optical isomers thereof.

Preferred in this aspect of the invention are compounds in which one of $A_1$ and $A_2$ is H, $A_5$ is H, $A_6$ is OH, $A_7$ and $A_8$ are $CH_3$ and $A_3A_4N$ together are a lactam.

The contents of U.S. Pat. Nos. 5,284,857 and 5,030,736 are herein incorporated by reference for their disclosure of particular compounds and their syntheses.

The invention also consists in a method of preparing a composition for use in modulation of hair growth in a human or other mammal by topical application, comprising the step of incorporating in a dermally acceptable formulation at least one of thienopyran compound, more particularly those herein defined.

In accordance with the present invention, compositions provided may be administered to human individuals or used as a veterinary medicine, particularly for other mammals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, eg decisions on dosage etc, is within the responsibility of general practitioners and other medical doctors.

Pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such an ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, tonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

When used for mammalian hair growth modulation, i.e. hair growth stimulation or hair growth inhibition, the thienopyran compounds may be administered to the skin topically, i.e. at the growth site. For this purpose a composition containing the active thienopyran compound or compounds is prepared, containing also appropriate dermally acceptable formulating ingredients, such as oil, emulsifying agent, skin permeation enhancer, liposomes, perfume, and a solvent (such as alcohol and propylene glycol).

All stereo isomers, including optical isomers, of any compounds disclosed herein are included within the invention.

An alkyl group herein is preferably lower alkyl. Lower alkyl means $C_{1-4}$ unless otherwise specified.

When a group or atom is described as substituted it may be substituted by any of OH, halogen, lower alkyl, alkoxy ($C_{1-4}$), nitro cyano and haloalkyl ($C_{1-4}$).

INTRODUCTION OF THE DRAWINGS

Examples of the invention will now be described, for illustration and without intention to limit the scope of the invention. In the drawings.

EXAMPLES

Figure 1A:
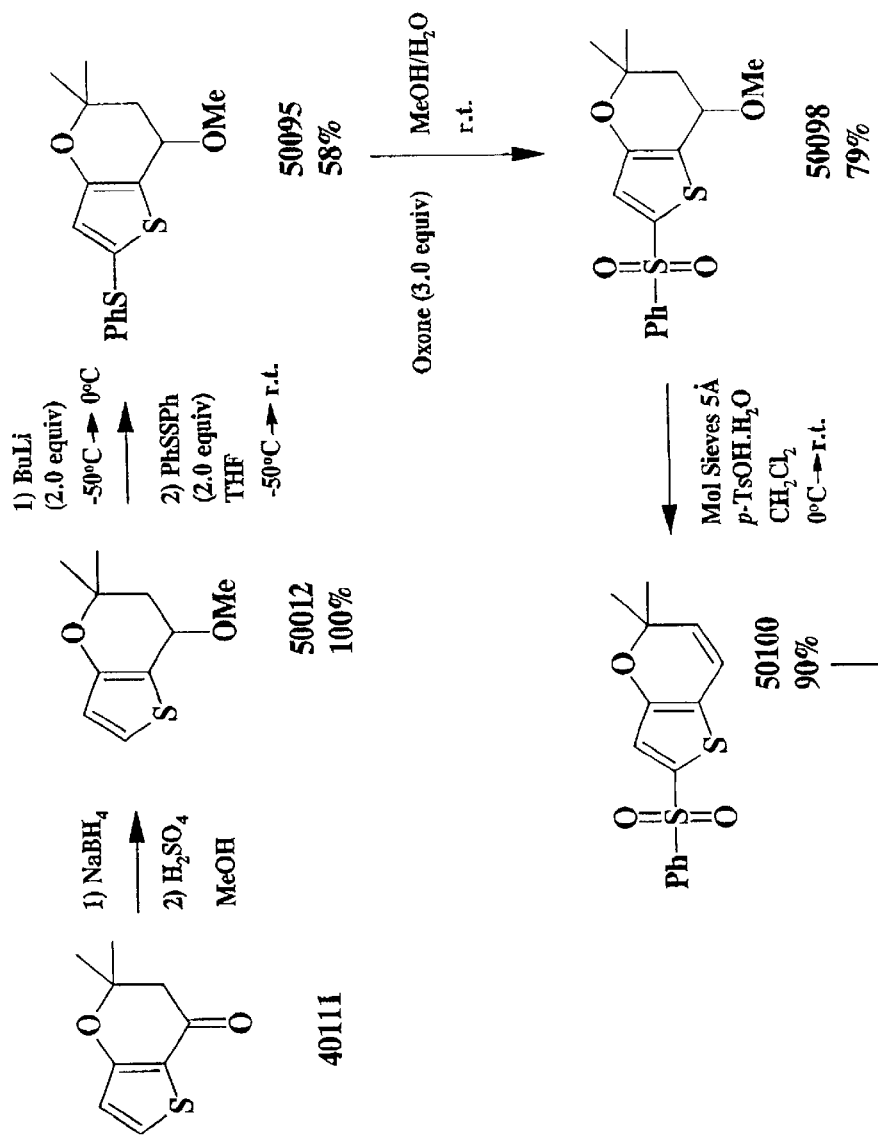
FIGS. 1A–1B and 1C–1D show a reaction scheme for making a series of compounds described in the Examples.
Figure 1B:
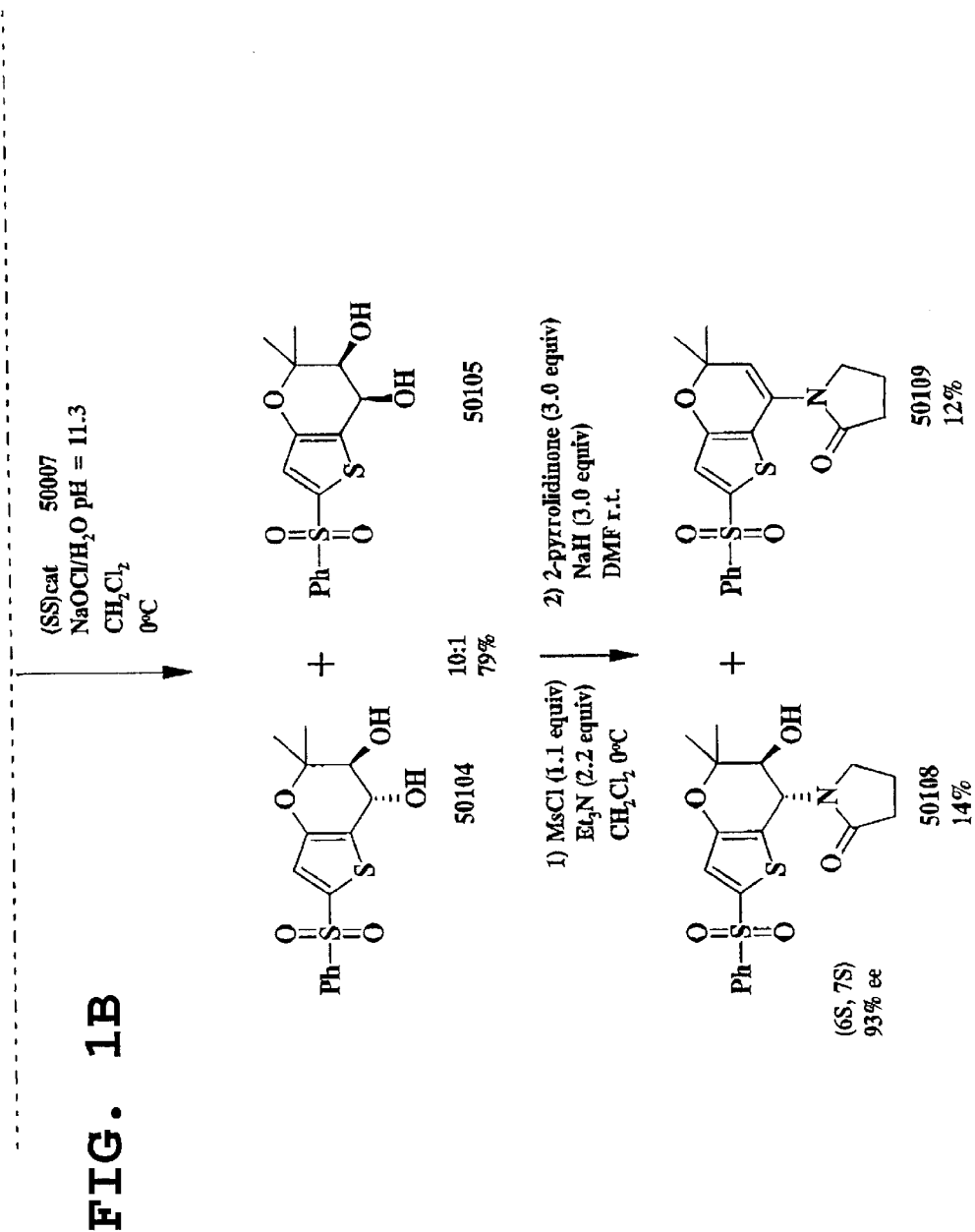
Figure 1C:
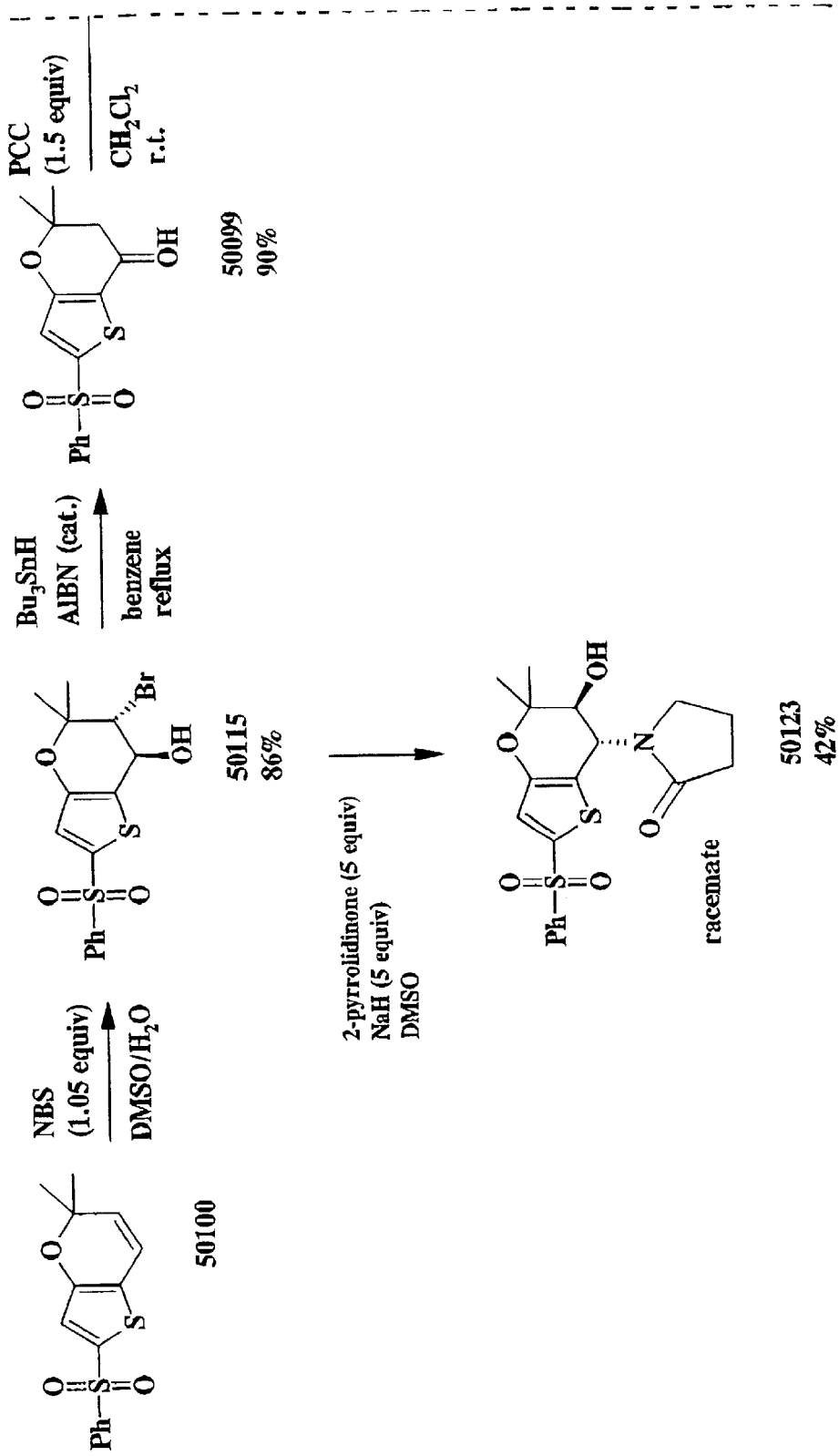
Figure 1D:
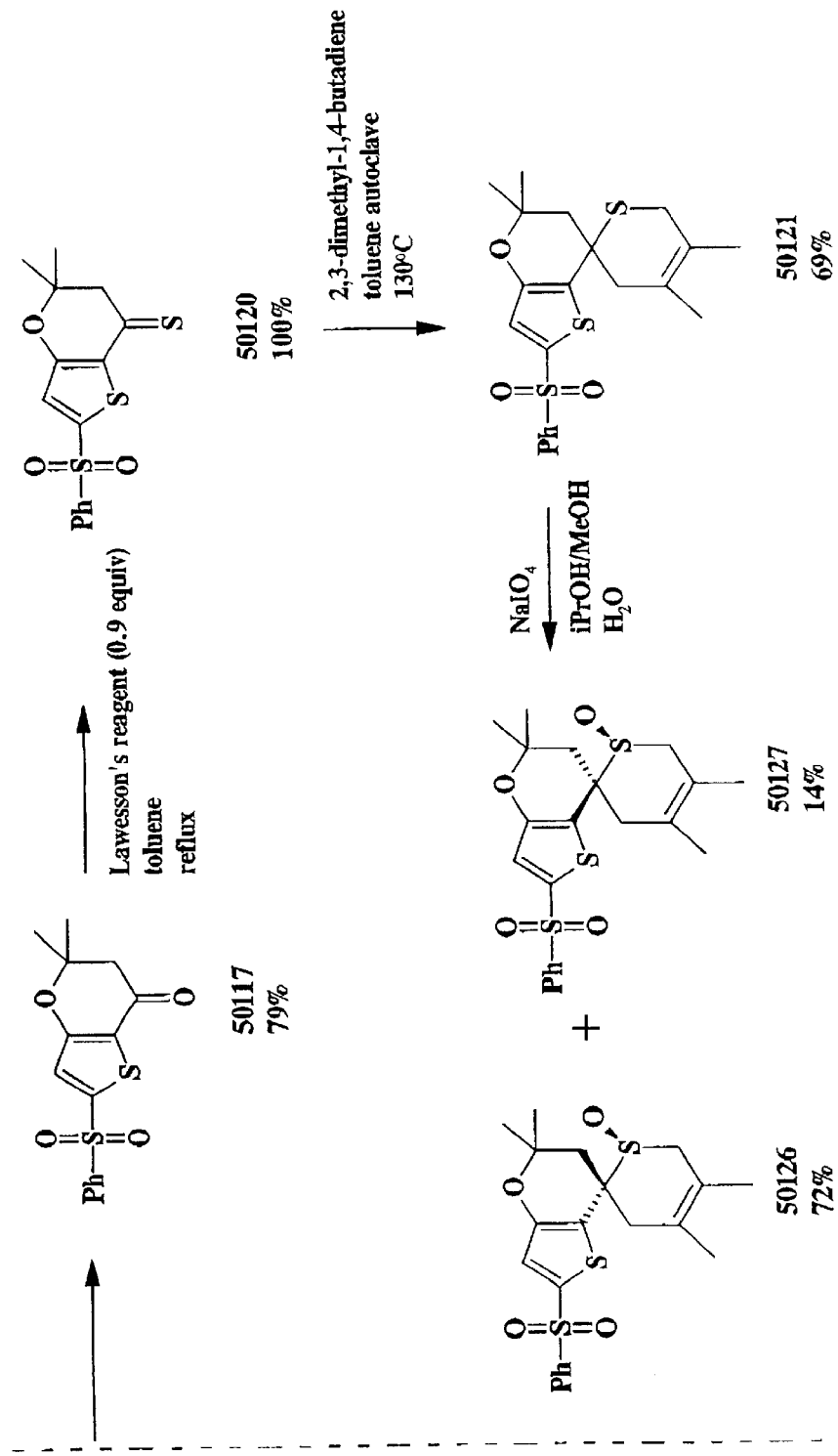

Table 1 summarises the compounds of the invention whose synthesis details are given below. Prior art compounds 11901 and 11903 (see above) are included. The compounds are identified by the internal reference numbers which are used by the inventors. In Table 1 the compounds are arranged not in numerical order but according to structural similarities. Table 1 also gives $IC_{50}$ values obtained in the $K^+$-stimulated isolated rat aorta test described below.

TABLE 1

Thienopyran base structures:

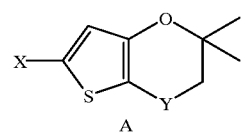

A

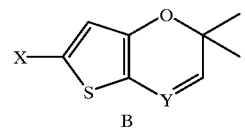

B

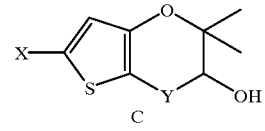

C

| Compound | Base Structure | X | Y | $IC_{50}$ ($\mu M$) |
|---|---|---|---|---|
| 11901 | C | CN | 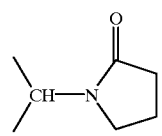 | 0.031 |

TABLE 1-continued

Thienopyran base structures:

A: X-substituted thieno[3,2-b]-2,2-dimethyl-2,3-dihydro-1,4-dioxine (saturated Y-CH2)

B: X-substituted thieno[3,2-b]-2,2-dimethyl-2H-1,4-dioxine (unsaturated Y=CH)

C: X-substituted thieno[3,2-b]-2,2-dimethyl-3-hydroxy-2,3-dihydro-1,4-dioxine (Y-CH(OH))

| Compound | Base Structure | X | Y | IC₅₀ (µM) |
|---|---|---|---|---|
| 11903 | C | CN | –CH(iPr)–N-pyrrolidin-2-one | 0.013 |
| 50063 | A | H | 2-methyl-1,3-dithiolan-2-yl | 10* |
| 50066 | A | CN | 2-methyl-1,3-dithiolan-2-yl | 10* |
| 50048 | A | H | 2-methyl-1,3-dithian-2-yl | 2.9 |
| 50057 | A | CN | 2-methyl-1,3-dithian-2-yl | 10* |
| 50049 | A | H | 2,3,6-trimethyl-3,6-dihydro-2H-thiopyran-2-yl | 10* |
| 50092 | A | CN | 2,3,6-trimethyl-3,6-dihydro-2H-thiopyran-2-yl | 10* |
| 50064 | A | H | 2-methyl-1,3-dithiolan-2-yl 1-oxide | 10* |
| 50065 | A | H | 2-methyl-1,3-dithiolan-2-yl 1-oxide | 30* |
| 50067 | A | CN | 2-methyl-1,3-dithiolan-2-yl 1-oxide | 100* |
| 50068 | A | CN | 2-methyl-1,3-dithiolan-2-yl 1-oxide | 30* |
| 50077 | A | H | 2-methyl-1,3-dithian-2-yl 1-oxide | See note 1 |

TABLE 1-continued
Thienopyran base structures:
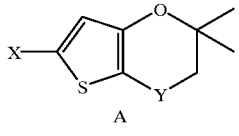
A
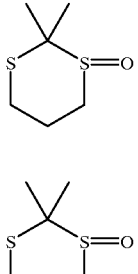
B
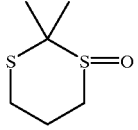
C
| Compound | Base Structure | X | Y | IC$_{50}$ ($\mu$M) |
|---|---|---|---|---|
| 50070 | A | H | 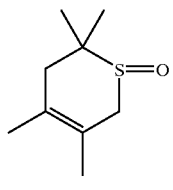 | See note 1 |
| 50076 | A | CN | 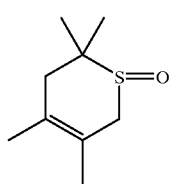 | See note 2 |
| 50074 | A | CN | 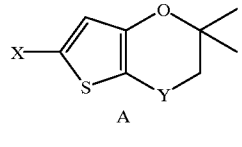 | See note 2 |
| 50054 | A | H | 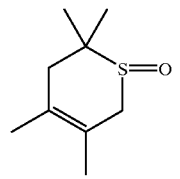 | 3* |
| 50055 | A | H | 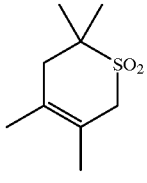 | 10* |
TABLE 1-continued
Thienopyran base structures:
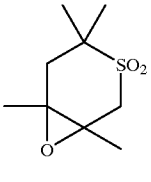
A
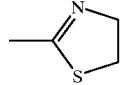
B
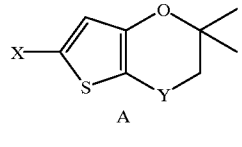
C
| Compound | Base Structure | X | Y | IC$_{50}$ ($\mu$M) |
|---|---|---|---|---|
| 50096 | A | CN | 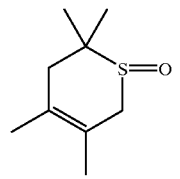 | 2.3 |
| 50097 | A | CN | 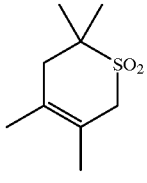 | 10* |
| 50110 | A | H | 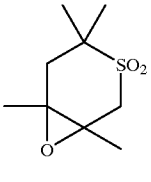 | 10 |
| 50111 | A | H | 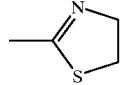 | 3.0 |
| 50133 | B |  |  | N/A |

TABLE 1-continued

Thienopyran base structures:

A, B, C (structures as shown)

| Compound | Base Structure | X | Y | IC$_{50}$ ($\mu$M) |
|---|---|---|---|---|
| 50040 | B | CN | 1-(prop-1-en-2-yl)pyrrolidin-2-one | N/A |
| 50106 | B | CN | 2-(prop-1-en-2-yl)-3,4-dimethyl-2,5-dihydrothiophene 1-oxide | N/A |
| 50174 | A | CF$_2$CF$_3$ | 1-isopropylpiperidin-2-one | N/A |
| 50061 | A | PO(OC$_2$H$_5$)$_2$ | 2-methyl-1,3-dithiane | N/A |
| 50062 | A | PO(OH)(OC$_2$H$_5$) | 2-methyl-1,3-dithiane | N/A |
| 50203 | A | SO$_2$(C$_6$H$_5$) | 2,2-dimethyltetrahydro-2H-thiopyran-4(3H)-one | N/A |
| 50204 | A | SO$_2$(C$_6$H$_5$) | 2,2-dimethyltetrahydro-2H-thiopyran-4(3H)-one | N/A |
| 50121 | A | SO$_2$(C$_6$H$_5$) | 2,2,4,5-tetramethyl-3,6-dihydro-2H-thiopyran | >100* |
| 50126 | A | SO$_2$(C$_6$H$_5$) | 2,2,4,5-tetramethyl-3,6-dihydro-2H-thiopyran 1-oxide | 6.3 |
| 50127 | A | SO$_2$(C$_6$H$_5$) | 2,2,4,5-tetramethyl-3,6-dihydro-2H-thiopyran 1-oxide | 7.4 |
| 50108 See note 3 | C | SO$_2$(C$_6$H$_5$) | 1-isopropylpyrrolidin-2-one | 0.018 |

TABLE 1-continued

Thienopyran base structures:

A

B

C

| Compound | Base Structure | X | Y | IC$_{50}$ ($\mu$M) |
|---|---|---|---|---|
| 50123 See note 3 | C | SO$_2$(C$_6$H$_5$) | 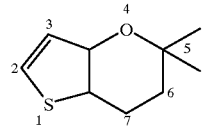 | 0.026 |
| 50109 | B | SO$_2$(C$_6$H$_5$) | | 0.24 |

IC$_{50}$ values given an asterisk (*) indicate that the compound showed low activity, so that solvent and time effects prevented calculation of an accurate IC$_{50}$ value. Only approximate values are given for these compounds.

Note 1: 15:85 mixture of the optically isomeric compounds 50077 and 50070 gave an IC$_{50}$ value of 10*.

Note 2: 20:80 mixture of the optically isomeric compounds 50076 and 50074 gave an IC$_{50}$ value of 10*.

Note 3: 50108 is one of the optical isomers of the formula given, in slightly impure form (see below). 50123 is a racemate of the two optical isomers of this formula.

N/A Not available.

K$^+$-stimulated Isolated Rat Aorta Test

Male rats weighing about 300 g are killed painlessly by a blow to the neck and quickly exsanguinated. The thoracic cavity is opened and the aorta is carefully resectioned. It is placed in a Petri dish filled with Krebs solution, and surrounding connective and fatty tissue is removed. Two rings are prepared. The rings are each suspended in an organ bath, They are attached at the bottom to a hook and at the top to an electrical force transducer which is able to measure precisely contractions of 0–10 grams in strength. The measured contractions are amplified by means of a bridge amplifier and recorded with a thermal plotter.

The organ baths are filled with Krebs solution at 37° C. through which an O$_2$/CO$_2$ mixture is bubbled thoroughly and which has the following composition (mmol/l): NaCl 118.4; KCl 4.7; CaCl$_2$ 2.5; KH$_2$PO$_4$ 1.2; MgSO$_4$ 1.2; NaHCO$_3$ 25; glucose 11.

The rings are stretched with a basic tone of about 0.5 g, After an equilibration time of about 30 minutes, the rings are caused to undergo contraction by depolarization (addition of 25 mM KCl to the organ bath). The contractions of the rings of aorta, triggered by the depolarization, quickly reach a plateau, As soon as this plateau is reached ("100% value"), the test substance is added to the organ bath, initially at low concentrations, for example 10$^{-8}$M, and then in increasing doses at regular intervals, until the contractions reduce or the final concentration of 10$^{-4}$M is reached. Each test substance is tested 2–4 times in this way.

For purposes of evaluation, the height of the contractions registered on the plotter paper is measured for each experiment after the action of each test concentration added. The IC$_{50}$ value can be calculated in this way in relation to the original height of contractions before the addition of substance (100%). IC$_{50}$ values are shown in Table 1 in $\mu$M.

Syntheses

The compounds of the invention in Table 1 were synthesized as follows. References are listed at the end of this description.

General

The ring numbering of the thienopyran ring structure of these compounds is

Infrared (IR) spectra were determined (KBr) using a FT-IR spectrophotometer and are reported in cm$^{-1}$. Proton nuclear magnetic resonance ($^1$H NMR) spectra were determined (with the solvent in brackets) using a Bruker ARX-400 (400 MHz) instruments. This machine was also used for $^{13}$C NMR (APT) spectra (100.6 MHz) or for special techniques (C,H COSY, H,H COSY). Chemical shifts are given in ppm downfield from tetramethylsilane. R$_f$ values were obtained by using thin-layer chromatography (TLC) on silica gel-coated aluminum sheets (Merck 60 F$_{254}$) with the indicated solvent (mixture). Flash chromatography was performed according to ref. 16 using silicagel KG60 and the indicated solvent (mixture). Melting points and boiling points are uncorrected. CH$_2$Cl$_2$ was distilled from P$_2$O$_5$ and kept under an atmosphere of dry nitrogen. Dry THF was distilled under a dry nitrogen atmosphere from KOH prior to use. Reactions under a nitrogen atmosphere were performed in flame-dried glassware. Standard syringe techniques were applied for the transfer of Lewis acids, dry solvents and reagents.

Reaction Schemes

The synthesis of the spiro dithiolane and dithiane compounds started with the reaction of ketone 40111 (see ref. 11 for synthesis of this) with 1,2-ethane- and 1,3-propanedithiol under Lewis acid conditions (ref. 1) as depicted in eq 1 and eq 2. 50063 and 50048 were isolated in 59% and 57% yield, respectively.

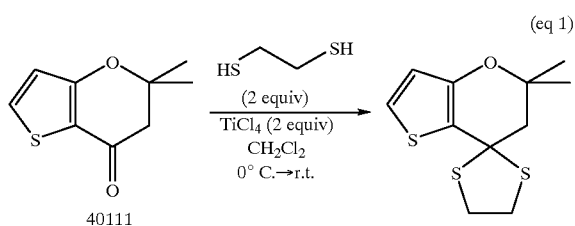
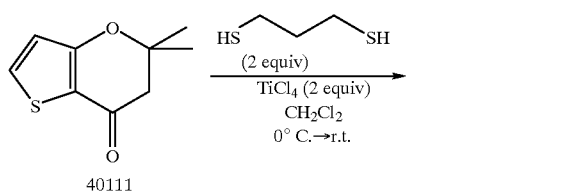
Introduction of a cyanogroup at the C-2 position of the thienopyran system by deprotonation (BuLi) and reaction with p-tosyl cyanide (ref. 2), gave the cyano compounds 50066 (eq 3) and 50057 (Scheme 1) in low yields (25% and 43%, respectively). S.M. is starting material.
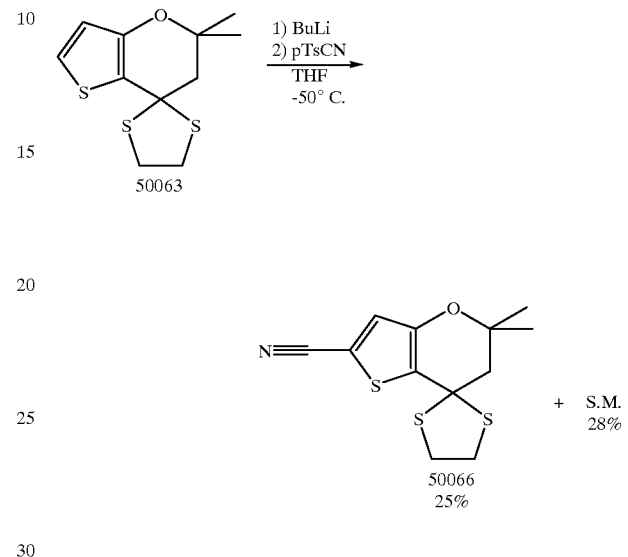
Scheme 1
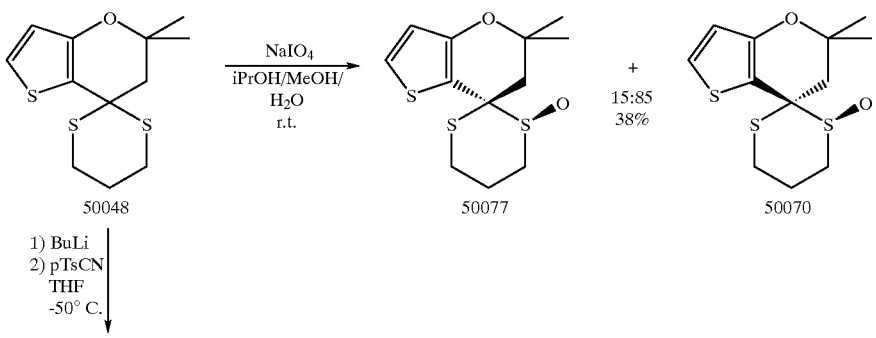
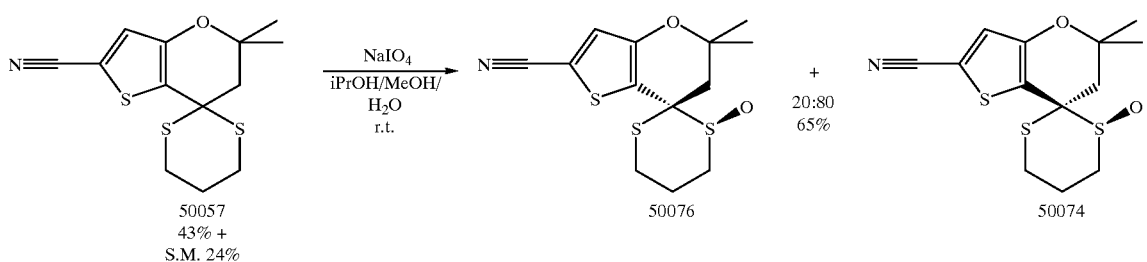

Oxidation (ref. 3) of one of the sulphur atoms in 50063 (Scheme 2) gave the two diastereomeric sulphoxides (ref. 4) 50064 (43%) and 50065 (10%). In a small amount the disulphoxide was formed which rearranged (ref. 4) to the dithiin 50071 (5% yield).

50048 (Scheme 1) was oxidized (ref. 3) to give an inseparable 85:15 mixture of 50070 and 50077 in 38% yield (ref. 5). Attempts to purify this mixture by crystallisation from petroleum ether failed. These two compounds were tested as a mixture.

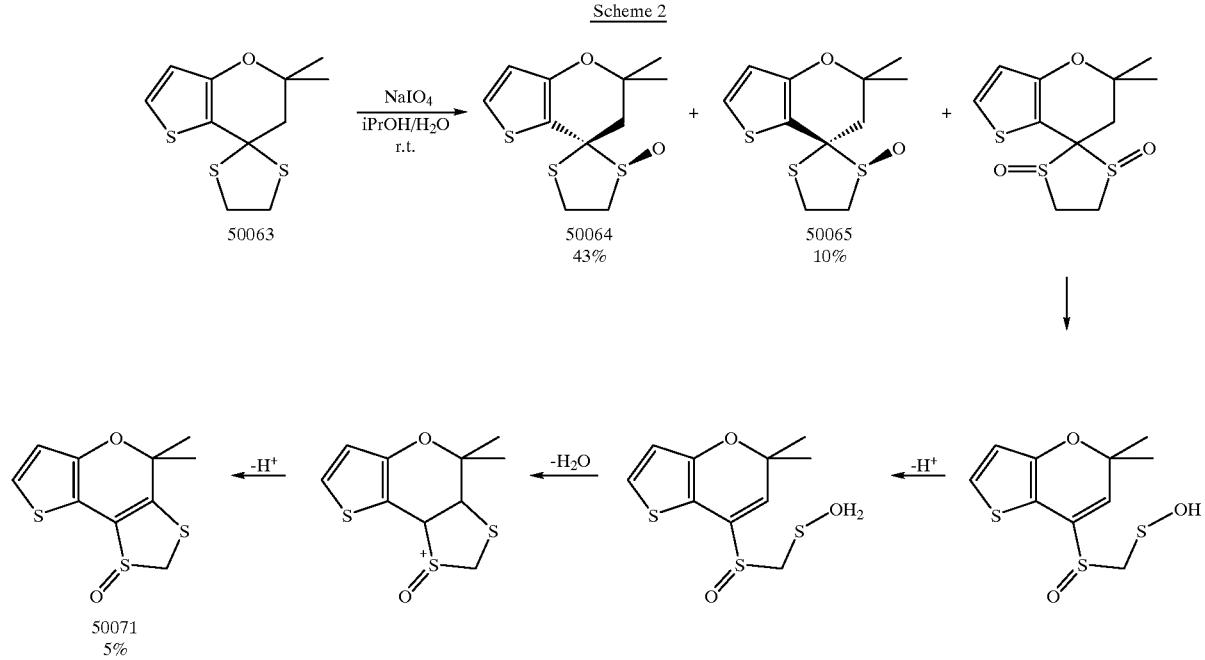

Oxidation (ref. 3) of 50066 (eq 4) gave 50067 and 50068 in 32% and 4% yield, respectively (55% starting material was recovered) (ref. 4).

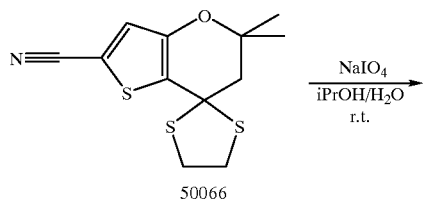

(eq 4)

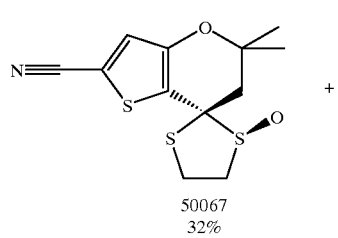

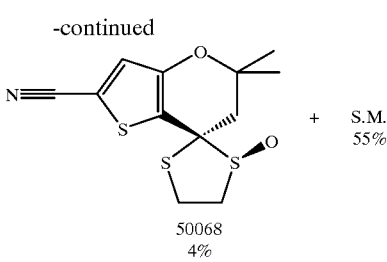

Oxidation (ref. 3) of 50057 (Scheme 1) gave, as with the oxidation of 50048, an inseparable 80:20 mixture of 50074 and 50076 in 65% yield (ref. 5). Attempts to purify this mixture by crystallisation from petroleum ether failed. These two compounds were also tested as a mixture.

Scheme 3

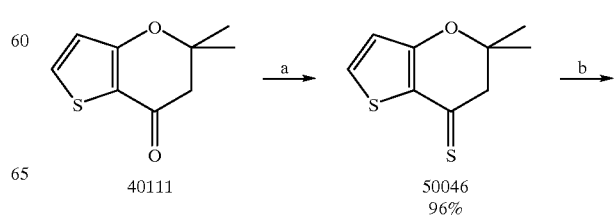

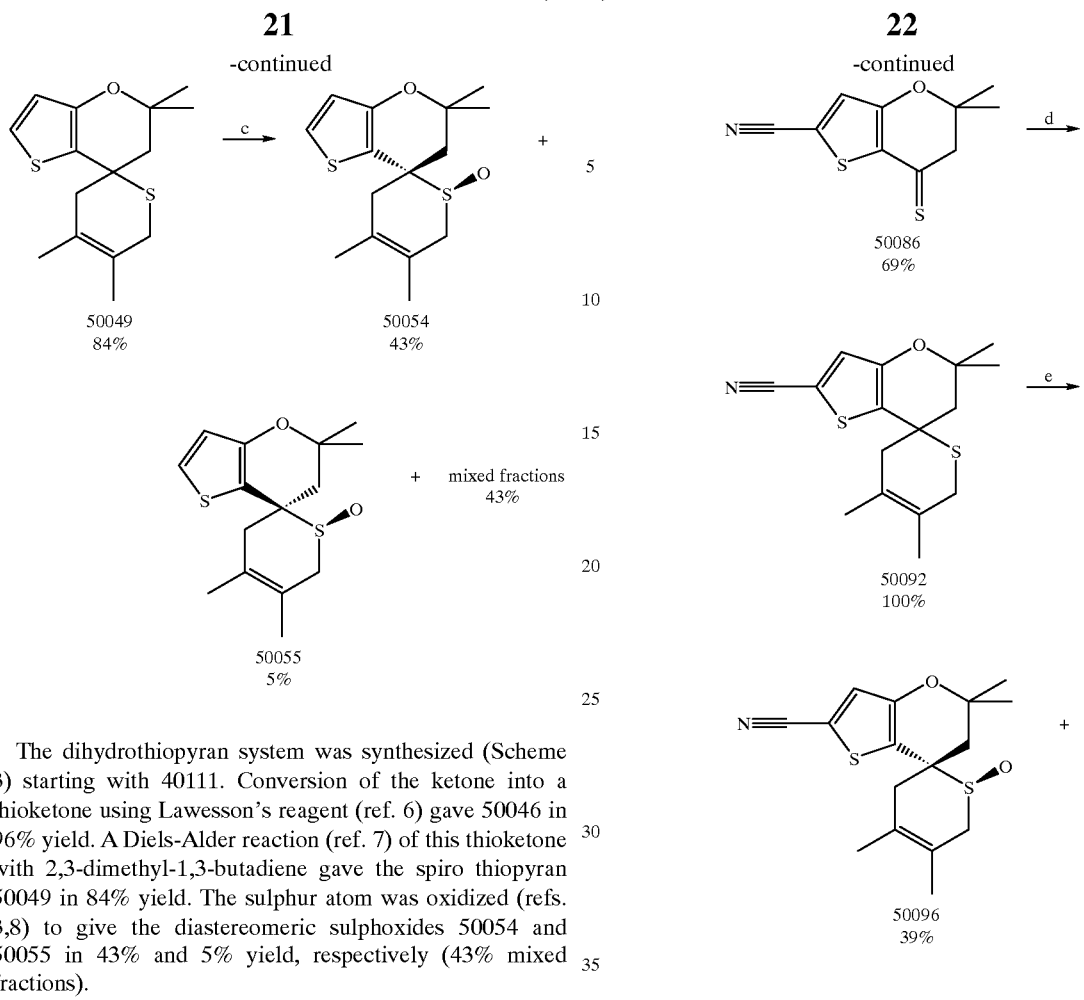

The dihydrothiopyran system was synthesized (Scheme 3) starting with 40111. Conversion of the ketone into a thioketone using Lawesson's reagent (ref. 6) gave 50046 in 96% yield. A Diels-Alder reaction (ref. 7) of this thioketone with 2,3-dimethyl-1,3-butadiene gave the spiro thiopyran 50049 in 84% yield. The sulphur atom was oxidized (refs. 3,8) to give the diastereomeric sulphoxides 50054 and 50055 in 43% and 5% yield, respectively (43% mixed fractions).

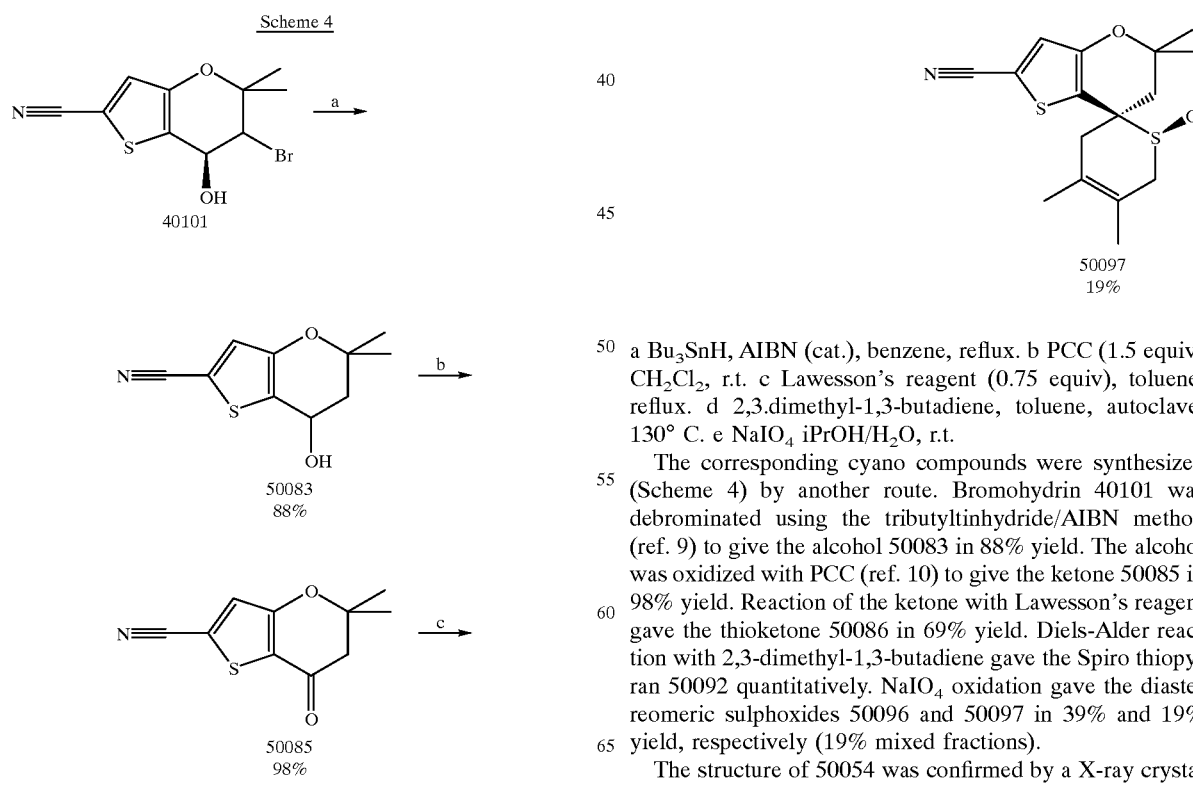

a Bu$_3$SnH, AIBN (cat.), benzene, reflux. b PCC (1.5 equiv) CH$_2$Cl$_2$, r.t. c Lawesson's reagent (0.75 equiv), toluene, reflux. d 2,3.dimethyl-1,3-butadiene, toluene, autoclave, 130° C. e NaIO$_4$ iPrOH/H$_2$O, r.t.

The corresponding cyano compounds were synthesized (Scheme 4) by another route. Bromohydrin 40101 was debrominated using the tributyltinhydride/AIBN method (ref. 9) to give the alcohol 50083 in 88% yield. The alcohol was oxidized with PCC (ref. 10) to give the ketone 50085 in 98% yield. Reaction of the ketone with Lawesson's reagent gave the thioketone 50086 in 69% yield. Diels-Alder reaction with 2,3-dimethyl-1,3-butadiene gave the Spiro thiopyran 50092 quantitatively. NaIO$_4$ oxidation gave the diastereomeric sulphoxides 50096 and 50097 in 39% and 19% yield, respectively (19% mixed fractions).

The structure of 50054 was confirmed by a X-ray crystal structure determination. The stereochemistry of the other sulphoxide compounds were concluded from their NMR Spectra in comparison with the NMR data of 50054 and 50055.

Synthesis Details and Compound Data

50040

5,5-Dimethyl-7-(2-oxo-1-pyrrolidinyl)-5H-thieno[3,2-b]pyran-2-carbonitrile

Under a nitrogen atmosphere, 11901 (0.510 g, 1.75 mmol) was dissolved into dichloromethane (25 ml) and placed in an ice bath. At 0° C., triethylamine (0.29 ml, 2.1 mmol) and methanesulfonyl chloride (0.16 ml, 2.1 mmol) were added. After 15 minutes the reaction mixture was allowed to warm up to room temperature. The reaction mixture was stirred for 1 h at room temperature. The mixture was washed with saturated sodium bicarbonate solution (10 ml). The organic layer was dried (MgSO$_4$) and concentrated in vacuo, The residual oil was taken up into dry THF (20 ml) and potassium t-butoxide (0.21 g, 1.9 mmol) was added. The reaction mixture was stirred for 2 h at room temperature. The reaction mixture was concentrated to dryness and taken up into dichloromethane (30 ml), The organic layer was washed with brine, dried (MgSO$_4$) and concentrated in vacuo. The residual oil was purified by flash chromatography (eluant: petroleum ether/EtOAc 1/1) to give 50040 as an off-white solid. $^1$H NMR (400 MHz, CDCl$_3$) 1.50 (s, 6 H), 2.16 (quintet, J=7.2 Hz, 2 H), 2.53 (t, J=8.0 Hz, 2 H), 3.67 (J=7.2 Hz, 2 H), 5.29 (s, 1 H), 7.03 (s, 1 H). $^{13}$C NMR (100 MHz, CDCl$_3$) 18.8, 27.5 (2×C), 31.6, 49.5, 80.0, 107.1, 114.5, 118.6 (2×C), 126.6, 129.2, 152.3, 174.6.

50046 (Intermediate)

6,7-Dihydro-5,5-dimethyl-5H-thieno[3,2-b]pyran-7-thione 40111 (30.0 g, 164.6 mmol) was dissolved in 1 l of toluene and Lawesson's reagent (33.3 g, 82.3 mmol) was added and the mixture was heated under reflux. After 1.5 h, the reaction mixture was allowed to cool down to room temperature and concentrated in vacuo. The residue was purified by chromatography (eluant: toluene, 450 g KG60, 1 l glass filter) to give 50046 (31.2 g, 157 mmol, 96%) as a red solid.

50048

6',7'-Dihydro-5',5'-dimethylspiro[1,3-dithiane-2,7'-5H-thieno[3,2-b]pyran]

Under a N$_2$ atmosphere, 40111 (11.62 g, 63.8 mmol) was dissolved into 180 ml of CH$_2$Cl$_2$ and 1,3-propanedithiol (15.0 ml, 149.4 mmol) was added. At room temperature TiCl$_4$ (18.5 ml, 168.3 mmol) was added dropwise. The reaction mixture turned brown. After stirring for 2 h a yellow solid precipitated. After 5 h, 1,3-propanedithiol (5.0 ml, 49.8 mmol) and TiCl$_4$ (5.0 ml, 45.5 mmol) was added and stirred overnight. The mixture was poured into 1 l of 5% NaOH. The water layer was extracted (3×) with CH$_2$Cl$_2$ and the collected organic layers were washed with 300 ml of a 5% KOH solution. The organic layer was dried (MgSO$_4$) and concentrated in vacuo to give 15.96 g of a yellow oil. This oil was purified over a 1 l G3 glass filter funnel charged with 500 g of silica gel KG60 and toluene as eluant to give 50048 (9.91 g, 36.4 mmol, 57%) as a light yellow solid, R$_f$=0.52 (toluene). Mp: 121–123° C. $^1$H NMR (400 MHz, CDCl$_3$) 1.45 (s, 6 H), 1.95–2.20 (m, 2 H, 2.73 (s, 2 H), 2.85–2.95 (m, 2 H), 3.10–3.25 (m, 2 H), 6.54 (d, J=5.4 Hz, 1 H), 7.17 (d, J=5.4 Hz, 1 H). $^{13}$C NMR (100 MHZ, CDCl$_3$, APT) 24.4, 27.8, 28.8, 45.0, 47.7, 77.3, 115.8, 118.7, 124.7, 151.6.

50049

3',6,6',7-Tetrahydro-4',5,5,5'-tetramethylspiro[5H-thieno[3,2-b]pyran-7,2'-2H-thiopyran]

A 135 cm$^3$ autoclave was charged with a solution of 50046 (8.23 g, 41.5 mmol) in 60 ml of toluene. To the stirred solution, 2,3-dimethyl-1,3-butadiene (10 ml, 7.27 g, 88.5 mmol) was added. The autoclave was closed and heated at 130° C. for 18 h. The reaction mixture was allowed to cool down to room temperature and concentrated in vacuo to give a red oil (11.22 g). This oil was purified over a 1 L G3 glass filter funnel charged with 350 g of silica gel KG60 with petroleum ether/EtOAc 15/1 as eluant to give a pure 50049 fraction (4.8 g, 17.1 mmol, 41%, light green solid) and a fraction contaminated with unreacted 50046 (5.0 g, 17.8 mmol, 43% light green/orange solid). Pure 50049 could be obtained by crystallization from petroleum ether/EtOAc. Rf=0.70 (toluene). Mp: 90–92° C. $^1$H NMR (400 MHz, CDCl$_3$) 1.41 (s, 3 H), 1.52 (s, 3 H), 1.69 (s, 3 H), 1.81 (s, 3 H), 2.00 (d, J=14.6 Hz, 1 H), 2.21 (d, J=14.6 Hz, 1 H), 2.43 (bd, J=15.6 Hz, 1 H), 2.48 (bd, J=15.6 Hz, 1 H), 3.22 (bd, J=15.6 Hz, 1 H), 3.34 (bd, J=15.6 Hz, 1 H), 6.56 (d, J=5.4 Hz, 1 H), 7.03 (d, J=5.4 Hz, 1 H). $^{13}$C NMR (100 MHz, CDCl$_3$) 18.6, 19.1, 26.7, 32.0, 39.6, 46.8, 49.2, 76.4, 117.6, 118.8, 122.9, 123.4, 126.4, 150.1.

50054 and 50055 rel-(1'R, 2'R)-3',6,6',7-Tetrahydro-4',5,5',5-tetramethylspiro[5H-thieno[3,2-b]pyran-7,2'-2H-thiopyran]-1'-oxide (50054)

rel-(1'R, 2'S)-3',6,6',7-Tetrahydro-4',5,5',5-tetramethylspiro[5N-thieno[3,2-b]pyran-7,2'-2H-thiopyran]-1'-oxide (50055)

50049 (2.00 g, 7.10 mmol) was dissolved in a mixture of 250 ml of methanol and 100 ml of isopropanol. The mixture was placed in an ice bath and at 0° C. a solution of NaIO$_4$ (1.56 g, 7.10 mmol) in 20 ml of water was added. The reaction mixture was allowed to warm up to room temperature. The reaction mixture became turbid. After stirring overnight, the white precipitation was filtered off and the filtrate was taken up in 500 ml of ethyl acetate. The organic layer was washed with brine, The water layer was extracted (3×) with 300 ml of ethyl acetate. The collected organic layers were washed with water then dried (MgSO$_4$) and concentrated in vacuo to give a yellow solid (2.1 g). This residue was purified by flash chromatography (eluant: EtOAc) to give 50055 (0.10 g, 0.34 mmol, 5%, white solid) and 50054 (0.90 g, 3.04 mmol, 43%, white solid) and a mixed fraction of 50054 and 50055 (0.90 g, 3.04 mmol, 43%, white solid). 50054: R$_f$=0.41 (EtOAc). Mp: 135–142° C. Anal. Cald for C$_{15}$H$_{20}$O$_2$S$_2$: C, 60.78; H, 6.8. Found: C, 60.6; H, 6.4. IR 1065 (S=O). $^1$H NMR (400 MHz, CDCl$_3$) 1.45 (s, 3 H), 1.55 (s, 3 H), 1.67 (d, J=15.0 Hz, 1 H), 1.74 (s, 3 H), 1.81 (s, 3 H), 1.93 (bd, J=17.5 Hz, 1 H), 2.64 (d, J=15.0 Hz, 1 H), 3.02 (bd, J=17.2 Hz, 1 H), 3.24 (bd, J=18,0 Hz, 1 H), 3.72 (bd, J=18.0 Hz, 1 H), 6.58 (d, J=5.5 Hz, 1 H), 7.08 (d, J=5.5 Hz, 1 H). $^{13}$C NMR (100 MHz, CDCl$_3$) 19.2, 20.5, 26.4, 30.0, 37.8, 39.2, 49.3, 53.5, 76.2, 107.5, 117.8, 119.2, 125.3, 126.7, 154.4. 50055: R$_f$=0.50 (EtOAC). Mp: 127–135° C. Anal. Cald for C$_{15}$H$_{20}$O$_2$S$_2$: C, 60.78; H, 6.8. Found: C, 60.8; H, 6.0. IR 1065 (S=O). $^1$H NMR (400 MHz, CDCl$_3$) 1.33 (s, 3 H), 1.39 (s, 3 H), 1.69 (s, 3 H), 1.69 (d, J=14.3 Hz, 1 H), 1.73 (s, 3 H), 1.90 (d, J=14.3 Hz, 1 H), 2.23 (bd, J=18.0 Hz, 1 H), 3.16 (bd, J=18.4 Hz, 1 H), 3.19 (bd, J=18.0 Hz, 1 H), 3.31 (bd, J=18.4 Hz, 1 H), 6.58 (d, J=5.4 Hz, 1 H), 7.13 (d, J=5.4 Hz, 1 H). $^{13}$C NMR (100 MHz, CDCl$_3$) 19.3, 20.4, 26.9, 29.0, 36.7, 38.8, 49.3, 53.1, 75.7, 111.5, 115.3, 118.4, 125.4, 125.9, 151.7.

50057

6',7'-Dihydro-5',5'-dimethylspiro[1,3-dithiane-2,7'-5H-thieno[3,2-b]pyran]-2'-carbonitrile Under a N$_2$-atmosphere, 50048 (115.7 mg, 0.425 mmol) was suspended in 5 ml of THF and placed in a CO$_2$/EtOH bath of −65° C. To the suspension BuLi (1.6 M solution in n-hexane, 0.7 ml, 1.1 mmol) was added. The reaction mixture became yellow/green. An amount of 50048 did not dissolve. The reaction mixture was allowed to warm up to −50° C. over a 2 h period. To the reaction mixture a solution of p-tosyl cyanide (130 mg, 0.717 mmol, Aldrich) in 2 ml of THF was added. The mixture turned red/brown. After 20 min the reaction mixture became turbid and was allowed to warm up to room temperature. After stirring for 3 h at room temperature, the mixture was taken up in CH$_2$Cl$_2$/water and filtered over celite. The organic layer was purified and the water layer extracted with CH$_2$Cl$_2$. The collected organic layers were dried (MgSO$_4$) and concentrated in vacuo to give 1.5 g of a red oil. The oil was purified by flash chromatography (eluant: petroleum ether/EtOAc 2/1) to give starting material (27.7 mg, 0.102 mmol, 24%) and 50057 (54.8 mg, 0.184 mmol, 43%) as a light brown solid. R$_f$=0.40 (toluene). Mp: 137–148° C. $^1$H NMR (400 MHz, CDCl$_3$) 1.45 (s, 6 H, 1.95–2.20 (m, 2 H) 2.72 (s, 2 H), 2.85–2.98 (m, 2 H), 3.10–3.20 (m, 2 H), 7.03 (s, 1 H). $^{13}$C NMR (100 MHz, CDCl$_3$) 24.0, 27.7, 28.7, 44.4, 47.5, 78.3, 108.1, 114.3, 124.7, 128.0, 150.8.

50061 and 50062

(6',7'-Dihydro-5',5'-dimethylspiro[1,3-dithiane-2,7'-5H-thieno[3,2-b]pyran])-2'-yl phosphonic acid diethylester (50061)

(6',7'-Dihydro-5',5'-dimethylspiro[1,3-dithiane-2,7'-5H-thieno[3,2-b]pyran])-2'-yl phosphonic acid ethylester (50062)

Under a nitrogen atmosphere, 50048 (0.50 g, 1.84 mmol) was suspended in 20 ml of THF and placed in a CO$_2$/EtOH bath of −55° C. To the suspension BuLi (1.6 M solution in n-hexane, 1.4 ml, 2.2 mmol) was added. The reaction mixture became light brown. The reaction mixture was allowed to warm up to −25° C. over a 1 h period. The reaction mixture was cooled to −50° C. and diethyl chlorophosphate (0.35 ml, 2.43 mmol) was added dropwise. The reaction mixture was allowed to warm up to room temperature and stirred overnight. The reaction mixture was poured into water (100 ml) and extracted (3×50 ml) with dichloromethane. The collected organic layers were dried (MgSO$_4$) and concentrated in vacuo. This residual oil was purified by flash chromatography (eluant: petroleum ether/EtOAc 1/1) to give 50061 (80 mg, 0.20 mmol, 11%, yellow oil), 50062 (30 mg, 0.08 mmol, 4%) and a 2:1 mixed fraction of 50061/50062 (70 mg, 9%) and starting material (300 mg, 60%).

50061: $^1$H NMR (400 MHz, CDCl$_3$) 1.33 (t, J=7.0 Hz, 6 H), 1.43 (s, 6 H), 1,95–2.20 (m, 2 H), 2.67 (s, 2 H), 2.95 (ddd, J=14.8, 5.7, 3.5 Hz, 2 H), 3.12 (ddd, J=15.0, 10.4, 3.2 Hz, 2 H), 4.05–4.25 (m, 4H), 7.03 (d, $^3J_{H,P}$=9.0 Hz, 1 H). $^{13}$C NMR (100 MHz, CDCl$_3$) 16.2 (d, $^3_{C,P}$=6.6 Hz), 24.2, 27.8, 28.7 (2×C), 44.6, 47.6, 62.8 (d, $^2J_{C,P}$=5.4 Hz), 77.7, 123.7 (d, $^1J_{C,P}$=225.4 Hz), 124.9 (d, $^3J_{C,P}$=7.0 Hz), 127.1 (d, $^2J_{C,P}$=12.1 Hz), 151.5 (d, $^3J_{C,P}$=21.1 Hz). 50062; $^1$H NMR (400 MHz, CDCl$_3$) 1.34 (t, J=7.0 Hz, 3 H), 1.43 (s, 6 H), 2.00–2.20 (m, 2 H), 2.66 (s, 2 H), 2.85– 3.15 (m, 4H), 4.05–4.25 (m, 2H), 7.04 (d, $^3J_{H,P}$=8.8 Hz, 1 H).

50063

6',7'-Dihyrdro-5',5'-dimethylspiro[1,3-dithiolane-2, 7'-5H-thieno[3,2-b]pyran]

Under a nitrogen atmosphere, a 500 ml 3-neck round bottom flask equipped with a stirring bar and a 50 ml dropping funnel was charged with 40111 (20.58 g, 112.9 mmol), 1,2-ethanedithiol (20.0 ml, 238 mmol) and 250 ml of CH$_2$Cl$_2$. The flask was placed in an ice bath and at 0° C. TiCl$_4$ (25.0 ml, 228 mmol) was added dropwise over a 5 min period, The reaction mixture became dark brown. The mixture was allowed to warm up to room temperature and stirred overnight. The dark brown reaction mixture with some yellow precipitation was poured, in portions, to 1.5 L of a 5% NaOH solution. The mixture became light yellow and a white solid precipitated in the water layer. Then 500 ml of CH$_2$Cl$_2$ was added and the mixture was stirred vigorously. The phases were separated and the water layer was extracted again with 250 ml of CH$_2$Cl$_2$. The collected organic layers were washed with 400 ml of water, then dried (MgSO$_4$) and concentrated in vacuo to give a yellow solid (~24 g). To the yellow solid petroleum ether 40/60 was added and a white solid was precipitated. The crystals were filtered off and washed with petroleum ether 40/60. The crystals were dried to give 50063 (9.99 g, 38.7 mmol) as a white crystalline solid. The filtrate was concentrated in vacuo to give 13.67 g of a yellow oil, This yellow oil was purified over a 2 L G3 glass filter funnel charged with 400 g of silica gel KG60 with toluene as eluant to give an additional amount of 50063 (7.30 g, 28.2 mol) as a crystalline light yellow solid. Total yield 50063 (17.29 g, 66.9 mmol, 59%). Mp: 84–86° C. R$_f$=0.51 (toluene). $^1$H NMR (400 MHz, CDCl$_3$) 1.44 (s, 6 H), 2.65 (s, 2 H), 3.39–3.45 (m, 2 H), 3.54–3.60 (m, 2 H), 6.43 (d, J=5.4 Hz, 1 H, 7.12 (d, J=5.4 Hz, 1 H). $^{13}$C NMR (100 MHz, CDCl$_3$), 27.1, 40.7, 52.9, 60.7, 77.4, 118.5, 119.9, 124.5, 151.2.

50064, 50065 and 50071 rel-(1S, 2S)-6',7'-Dihydro-5',5'-dimethylspiro[1,3-dithiolane-2,7'-5H-thieno[3,2-b]pyran]-1-oxide (50064)

rel-(1S, 2R)-6',7'-Dihydro-5',5'-dimethylspiro[1,3-dithiolane-2,7'-5H-thieno[3,2-b]pyran]-1-oxide (50065)

2,3-Dihydro-5,5-dimethyl-5H-thieno[3',2':2,3]pyran [5,4-b]dithiin-1-oxide (50071)

50063 (2.00 g, 7.70 mmol) was dissolved in a mixture of 250 ml of methanol and 100 ml of isopropanol. The mixture was placed in an ice bath and at 0° C. a solution of NaIO$_4$ (1.70 g, 7.70 mmol) in 20 ml of water was added. The reaction mixture was allowed to warm up to room temperature. The reaction mixture became turbid. After stirring overnight, the white precipitation was filtered off and the filtrate was dissolved into 300 ml of ethyl acetate. The organic layer was washed with 500 ml of brine. The water layer was washed (3×) with 300 ml of ethyl acetate. The collected organic layers were dried (MgSO$_4$) and concentrated in vacuo to give 2.4 g of a brown oil. This residue was purified by flash chromatography (eluant EtOAc) to give 50064 (0.90 g, 3.28 mmol, 43%, light yellow crystals) and 50071 (0.10 g, 0.37 mmol, 5%, light brown crystals). A fraction with pure 50065 (0.20 g, 0.73 mmol, 10%) epimerized during concentration in vacuo to give a 28:72 mixture of 50064 and 50065. This fraction wag purified by flash chromatography (eluant: EtOAc) to give pure 50065 (29 mg, 0.11 mmol, 1.5%) and a mixed fraction (0.13 g 0.47 mmol, 6%, 50064:50065 1:5).

50064: $^1$H NMR (400 MHz, CDCl$_3$) 1.49 (s, 3 H), 1.50 (s, 3 H), 2.27 (d, J=15.2 Hz,1 H), 2.92 (d, J=15.2 Hz, 1 H), 3.45–3.60 (m, 3 H), 3.82–3.95 (m, 1 H), 6.57 (d, J=5.6 Hz, 1 H), 7.19 (d, J=5.6 Hz, 1 H). $^{13}$C NMR (100 MHz, CDCl$_3$). 25.8, 28.3, 31.8, 38.7, 54.8, 73.6, 77.1, 111.7, 119.6, 125.6, 152.7.

50065: $^1$H NMR (400 MHz, CDCl$_3$) 1.41 (s, 3 H), 1.44 (s, 3 H), 2.23 (d, J=14.6 Hz, 1 H), 2.27 (d, J=14.6 Hz, 1 H), 3.21 (ddd, J=13.8, 10.1, 7.6 Hz, 1 H), 3.37–3.50 (m, 2 H), 3.92 (ddd, J=10.8, 9.4, 6.2 Hz, 1 H), 6.57 (d, J=5.5 Hz, 1 H), 7.27 (d, J=5.5 Hz, 1 H). $^{13}$C NMR (100 MHz, CDCl$_3$) 27.0, 27.8, 32.7, 46.2, 54.3, 75.2, 76.4, 106.1, 118.2, 128.2, 153.7.

50071: Mp: 110–114° C.

50066

6',7'-Dihydro-5',5'-dimethylspiro[1,3-dithialane-2,7'-5H-thieno[3,2-b]pyran]-2'-carbonitrile Under a N$_2$-atmosphere, 50063 (4.40 g, 17.0 mmol) was dissolved in 300 ml of THF and placed in a CO$_2$/EtOH bath of −50° C. To the suspension BuLi (1.6 M solution in n-hexane, 13.2 ml, 20.8 mmol) was added. The reaction mixture became brown. The reaction mixture was allowed to warm up to −30° C. over a 1.5 h period. The reaction mixture was cooled down to −50° C. and p-tosyl cyanide (3.96 g, 20.5 mmol, Aldrich) was added portion wise. After 30 min the reaction mixture was allowed to warm up to 0° C. After stirring for 1.5 h, the reaction mixture was poured into 1 L of water and extracted (3×) with 300 ml of CH$_2$Cl$_2$. The collected organic layers were washed with water then dried (MgSO$_4$) and concentrated in vacuo to give 5.5 g of a red oil. The oil was purified by chromatography over a 1 L G3 glass filter funnel charged with 365 g of silica gel KG60 with toluene as eluant to give starting material (1.25 g, 4.83 mmol, 28%) and 50066 (1.20 g, 4.23 mmol, 25%) as a orange solid. R$_f$=0.47 (toluene). $^1$H NMR (400 MHz, CDCl$_3$) 1.43 (s, 6 H), 2.63 (s, 2 H), 3.40–3.60 (m, 4 H), 6.93 (s, 1 H). $^{13}$C NMR (100 MHz, CDCl$_3$) 27.0, 41.1, 52.1, 59.4, 78.4, 107.9, 114.4, 128.0, 129.5, 150.3.

50067 and 50068 rel-(1S, 2S)-6',7'-Dihydro-5',5'-dimethylspiro[1,3-dithiolane-2,7'-5H-thieno[3,2-b]pyran]-2'-carbonitrile-1-oxide (50067)

rel-(1S, 2R)-6',7'-Dihydro-5',5'-dimethylspiro[1,3-dithiolane-2,7'-5H-thieno[3,2-b]pyran]-2'-carbonitrile-1-oxide (50068)

50066 (0.27 g, 0.96 mmol) was dissolved in a mixture of 50 ml of methanol and 25 ml of isopropanol. The mixture was placed in an ice bath and at 0° C. a solution of NaIO$_4$ (0.21 g, 0.96 mmol) in 2 ml of water was added. The reaction mixture was allowed to warm up to room temperature. The reaction mixture became turbid. After stirring overnight, the white precipitation was filtered off and the filtrate was dissolved into 300 ml of CH$_2$Cl$_2$. The organic layer was washed with 200 ml of water then dried (MgSO$_4$) and concentrated in vacuo to give a light yellow solid. The residue was purified by flash chromatography (eluant: EtOAc) to give starting material (149.7 mg, 0.528 mmol, 55%), 50067 (92.3 mg, 0.308 mmol, 32%, light brown crystals) and 50068 (11.0 mg, 0.037 mmol, 4%, light brown crystals).

50067: R$_f$=0.63 (EtOAc). Mp: 116–122° C. IR 2204 (CN), 1060 (S=O). $^1$H NMR (400 MHz, CDCl$_3$) 1.50 (s, 3 H), 1.53 (s, 3 H), 2.27 (d, J=15.2 Hz, 1 H), 2.32 (d, J=15.2 Hz, 1 H), 3.40–3.65 (m, 3 H), 3.98–4.07 (td, J=11.2, 4.9 Hz, 1 H), 7.00 (s, 1 H). $^1$H NMR (400 MHz, DMSO-d6) 1.45 (s, 6 H), 2.38 (d, J=15.1 Hz, 1 H), 2.68 (d, J=15.1 Hz, 1 H), 3.45–3.70 (m, 4 H), 7.61 (s, 1 H). $^{13}$C NMR (100 MHz, CDCl$_3$). 26.0, 28.1, 32.0, 38.2, 55.2, 72.3, 78.2, 109.2, 113.7, 120.3, 128.8, 152.0.

50068: R$_f$=0.33 (EtOAc). $^1$H NMR (400 MHz, CDCl$_3$) 1.44 (s, 3 H), 1.46 (s, 3 H), 2.27 (d, J=14.7 Hz, 1 H), 2.32 (d, J=14.7 Hz, 1 H), 3.15–3.25 (m, 1 H), 3.45–3.60 (m, 2 H), 3.98–4.07 (m, 1 H), 7.07 (s, 1 H). $^1$H NMR (400 MHz, DMSO-d6) 1.36 (s, 3 H), 1.39 (s, 3 H), 2.40 (d, J=15.0 Hz, 1 H), 2.46 (d, J=15.0 Hz, 1 H), 3.45–3.65 (m, 3 H), 3.70–3.80 (m, 1 H), 7.57 (s, 1 H). $^{13}$C NMR (100 MHz, CDCl$_3$) 26.8, 27.6, 33.7, 45.9, 54.7, 74.7, 77.3, 111.4, 114.1, 115.3, 127.0, 152.6.

50070 and 50077 rel-(1S, 2R)-6',7'-Dihydro-5',5'-dimethylspiro[1,3-dithiane-2,7'-5H-thieno[3,2-b]pyran]-1-oxide (50070)

rel-(1S, 2S)-6',7'-Dihydro-5',5'-dimethylspiro[1,3-dithiane-2,7'-5H-thieno[3,2-b]pyran]-1-oxide (50077)

50048 (2.00 g, 7.34 mmol) was dissolved in a mixture of 100 ml of methanol and 250 ml of isopropanol. The mixture was placed in an ice bath and at 0° C. a solution of NaIO$_4$ (1.60 g, 7.48 mmol) in 20 ml of water was added. The reaction mixture was allowed to warm up to room temperature. The reaction mixture became turbid. After stirring overnight, the white precipitation was filtered off and the filtrate was dissolved into 300 ml of ethyl acetate. The organic layer was washed with 500 ml of brine. The water layer was washed (3×) with 300 ml of ethyl acetate. The collected organic layers were dried (MgSO$_4$) and concentrated in vacuo to give 2.1 g of an orange oil. This residue was purified by flash chromatography (eluant EtOAc) to give a mixture of 50070 and 50077 (0.80 g, 2.77 mmol, 38%). This mixture was crystallized from petroleum ether 40/60 to give a light green crystalline solid (0.08 g) which was one spot on TLC and according to $^1$H NMR a 85:15 mixture of 50070 and 50077.

50070: $^1$H NMR (400 MHz, CDCl$_3$) 1.53 (s, 3 H), 1.57 (s, 3 H), 2.19 (d, J=14.4 Hz, 1 H), 2.35–2.45 (m, 2 H), 2.45–2.55 (m, 1 H), 2.67 (d, J=14.4 Hz, 1 H), 2.65–2.80 (m,

1 H), 2.80–2.95 (m, 1 H), 3.05–3.15 (m, 1 H), 6.57 (d, J=5.3 Hz, 1 H), 7.24 (d, J=5.3 Hz, 1 H). $^{13}$C NMR (100 MHz, CDCl$_3$) 25.7, 27.3, 29.0, 29.6, 30.0, 48.6, 60.5, 76.6, 109.0, 119.5, 126.4, 155.0.

50077: $^1$H NMR (400 MHz, CDCl$_3$) [940104/1006] isolated signals: 1.50 (s, 3 H, CH$_3$), 2.08 (d, J=14.4 Hz, 1 H), 7.01 (d, J=5.3 Hz, 1 H), 7.25 (d, J=5.3 Hz, 1 H). $^{13}$C NMR (100 MHz, CDCl$_3$) isolated signals: 43.3, 39.4, 59.0, 76.1, 118.3, 127.3.

50074 and 50076 rel-(1S, 2R)-6',7'-Dihydro-5',5'-dimethyl-1-oxospiro [1,3-dithiane-2,7'-5H-thieno[3,2-b]pyran]-2'-carbonitrile (50074)

rel-(1S, 2S)-6',7'-Dihydro-5',5'-dimethyl-1-oxospiro [1,3-dithiane-2,7'-5H-thieno[3,2-b]pyran]-2'-carbonitrile (50076)

50057 (60 mg, 0.20 mmol) was dissolved in a mixture of 40 ml of methanol and 10 ml of isopropanol. The mixture was placed in an ice bath and at 0° C. a solution of NaIO$_4$ (50 mg, 0.23 mmol) in 0.5 ml of water was added. The reaction mixture was allowed to warm up to room temperature. The reaction mixture became turbid. After stirring overnight, the white precipitation was filtered off and the filtrate was concentrated in vacuo. The residue was purified by flash chromatography to give starting material (10 mg) and according to $^1$H NMR a 80:20 mixture of 50070 and 50077 (41.1 mg, 0.13 mmol, 65%) as a yellow crystalline solid (one spot on TLC). R$_f$=0.18 (EtOAc).

50074: $^1$H NMR (400 MHz, CDCl$_3$) 1.51 (s, 3 H, CH$_3$), 1.57 (s, 3 H, CH$_3$), 2.23 (d, J=14.5 Hz, 1 H), 2.35–2.45 (m, 2 H), 2.50–2.60 (m, 1 H), 2.67 (d, J=14.5 Hz, 1 H), 2.65–2.80 (m, 1 H), 2.80–2.95 (m, 1 H), 3.10–3.20 (m, 1 H), 7.04 (s, 1 H). $^{13}$C NMR (100 MHz, CDCl$_3$) 25.4, 27.2, 29.0, 29.1, 29.8, 48.8, 60.1, 77.6, 110.0, 113.9, 117.9, 128.6, 154.1.

50076: $^1$H NMR (400 MHz, CDCl$_3$) isolated signals: 1.48 (s, 3 H), 1.50 (s, 3 H), 2.6 (d, J=14.4 Hz, 1 H), 7.05 (s, 1 H). $^{13}$C NMR (100 MHz, CDCl$_3$) 25.8, 26.1, 29.1, 29.6, 38.8, 42.8, 59.1, 77.6, 110.8, 114.0, 117.7, 127.1, 151.8.

50083 (Intermediate)

6,7-Dihydro-7-hydroxy-5,5-diethyl-5H-thieno[3,2-b] pyran-2-carbonitrile 40101 (6.50 g, 22.6 mmol) was dissolved in 1 L of benzene at 30° C. To the solution AIBN (0.15 g, 0.91 mmol) and tributyltin hydride (6.5 ml, 7.15 g, 24.7 mmol) were added and the mixture was heated under reflux. After 1 h, the reaction mixture was allowed to cool down to room temperature and concentrated in vacuo to give a yellow oil. This oil was purified by flash chromatography (eluant: petroleum ether/EtOAc 2/1) to give 50083 (4.19 g, 20.0 mmol, 88%) as a light yellow solid.

50085 (Intermediate)

6,7-Dihydro-5,5-dimethyl-7-oxo-5H-thieno[3,2-b] pyran-2-carbonitrile

Under a N$_2$ atmosphere, PCC (6.10 g, 29.3 mmol) was dissolved in 95 ml of CH$_2$Cl$_2$ and a solution of 50083 (4.10 g, 19.6 mmol) in 100 ml of CH$_2$Cl$_2$ was added. The orange suspension turned black. After stirring for 1 h, 1 L of diethyl ether was added and the mixture was filtered off over celite and concentrated in vacuo to give a brown solid. The solid was purified by flash chromatography (eluant petroleum ether/EtOAc 2/1) to give 50085 (3.96 g, 19.1 mmol, 98%) as a light yellow solid.

50086 (Intermediate)

6,7-Dihydro-5,5-dimethyl-7-thio-5H-thieno[3,2-b] pyran-2-carbonitrile 50085 (2.00 g, 9.70 mmol) was dissolved in 100 ml of toluene and Lawesson's reagent (1.90 g, 4.80 mmol) was added and the mixture was heated under reflux. After 1.5 h, another portion of Lawesson's reagent (1.90 g, 4.80 mmol) was added. After 20 min the reaction mixture was allowed to cool down to room temperature and concentrated In vacuo. The residue was purified by flash chromatography (eluant: petroleum ether/EtOAc 3/1) to give 50086 (1.50 g, 6.72 mmol, 69%) as a green solid.

50092

3',6,6',7-Tetrahydro-4',5,5,5'-tetramethylspiro[5H-thieno[3,2-b]pyran-7,2'-2H-thiopyran]-2-carbonitrile A 135 cm$^3$ autoclave was charged with a solution of 50086 (1.00 g, 4.50 mmol) in 50 ml of toluene. To the solution 2,3-dimethyl-1,3-butadiene (0.70 g, 9.00 mmol) was added. The autoclave was closed and heated at 130° C. for 18 h. The reaction mixture was allowed to cool down to room temperature and concentrated in vacuo to give 50092 (1.37 g 4.50 mmol) as a orange solid. Crystallisation from petroleum ether/EtOAc gave 1.10 g of 50092 as a light yellow solid. R$_f$=0.51 (petroleum ether/EtOAc 10/1). Mp: 148–149° C. IR 2204. $^1$H NMR (400 MHz, CDCl$_3$) 1.41 (s, 3 H) 1.49 (s, 3 H), 1.69 (s, 3 H), 1.82 (s, 3 H), 2.04 (d, J=14.8 Hz, 1 H), 2.18 (d, J=14.8 Hz, 1 H), 2.24 (d, J=16.6 Hz, 1 H), 2.57 (d, J=16.6 Hz, 1 H), 3.17 (d, J=17.5 Hz, 1 H), 3.37 (d, J=17.5 Hz, 1 H), 7.03 (s, 1 H). $^{13}$C NMR (100 MHz, CDCl$_3$) 19.1, 20.9, 26.8, 29.7, 31.8, 39.3, 47.1, 48.2, 77.2, 106.4, 114.7, 124.5, 126.2, 126.3, 127.9, 149.3.

50096 and 50097 rel-(1'R, 2'R)-3',6,6',7-Tetrahydro-4',5,5',5-tetramethyl-1'-oxospiro[5H-thieno[3,2-b]pyran-7,2'-2H-thiopyran-2-carbonitrile (50096)

rel-(1'R, 2'S)-3',6,6',7-Tetrahydro-4',5,5',5-tetramethyl-1'-oxospiro[5H-thieno[3,2-b]pyran-7,2'-2H-thiopyran]-2-carbonitrile (50097)

50092 (0.50 g, 1.60 mmol) was dissolved in a mixture of 100 ml of methanol and 50 ml of isopropanol. The mixture was placed in an ice bath and at 0° C. a solution of NaIO$_4$ (0.35 g, 1.60 mmol) in 10 ml of water was added. The reaction mixture was allowed to warm up to room temperature. The reaction mixture became turbid. After stirring for 3 days, the white precipitation was filtered off and the filtrate was dissolved into 300 ml of CH$_2$Cl$_2$. The organic layer was washed (3×) with 200 ml of water then dried (MgSO$_4$) and concentrated in vacuo to give 0.6 g of a light yellow solid. The residue was purified by flash chromatography (eluant: EtOAc) to give starting material (0.08 g, 0.26 mmol, 16%) and 50097 (0.050 g, 0.156 mmol, 10%, white solid) and 50096 (0.20 g, 0.62 mmol, 39%, white solid) and a mixed fraction of 50096 and 50097 (0.10 g, 0.31 mmol, 19%).

50096: R$_f$=0.48 (EtOAc). Mp: 179–183° C. $^1$H NMR (400 MHz, CDCl$_3$) 1.45 (s, 3 H), 1.53 (s, 3 H), 1.68 (d, J=15.2 Hz, 1 H), 1.75 (s, 3 H), 1.83 (s, 3 H), 1.94 (d, J=17.4 Hz, 1 H), 2.67 (d, J=15.2 Hz, 1 H), 3.04 (d, J=17.4 Hz, 1 H), 3.27 (d, J=18.4 Hz, 1 H), 3.63 (d, J=18.4 Hz, 1 H), 7.05 (s, 1 H). $^{13}$C NMR (100 MHz, CDCl$_3$) 19.2, 20.6, 26.3, 29.7, 37.6, 38.5, 49.7, 53.9, 77.3, 109.0, 113.9, 116.0, 119.0, 127.0, 128.3, 153.6.

50097: R$_f$=0.57 (EtOAc). Mp: 145–150° C. $^1$H NMR (400 MHz, CDCl$_3$) 1.37 (s, 3 H), 1.43 (s, 3 H), 1.76 (s, 3 H), 1.78 (d, J=14.5 Hz, 1 H), 1.79 (s, 3 H), 1.98 (d, J=14.5 Hz, 1 H), 2.29 (d, J=17.4 Hz, 1 H), 3.13 (d, J=17.4 Hz, 1 H), 3.27 (d, J=18.3 Hz, 1 H), 3.36 (d, J=18.3 Hz, 1 H), 7.10 (s, 1 H). $^{13}$C NMR (100 MHz, CDCl$_3$) 19.2, 20.4, 26.8, 28.8, 36.9, 38.3, 49.1, 53.6, 77.3, 109.0, 114.2, 115.9, 120.0, 125.6, 127.4, 151.2.

Another group of compounds with phenylsulphonyl at the 2-position within the invention was synthesised by the routes shown in FIGS. 1A–1B and 1C–1D. This scheme started with ketone 40111 (ref. 11). NaBH$_4$ reduction (ref. 12) of 40111 gave the alcohol 40112 in situ which was converted to the methoxy compound under acidic conditions to give 50012 in quantitative yield. Deprotonation with BuLi (−50→0° C.) and reaction with diphenyl disulphide (ref. 13) gave on large scale (~100 mmol) the thioether 50095 in 58% yield. On smaller scale the yield was 79%. A major impurity was the corresponding alcohol of 50095 which was formed during work-up. When instead of 2 equiv BuLi and PhSSPh, 1.2 equiv were used, the yield dropped. Oxidation (ref. 14) of the phenylthio group with Oxone® gave the phenylsulphonyl compound 50098 in 79% yield. Elimination of the methoxy group under acidic conditions (ref. 12) gave 50100 in 90% yield. Purification of 50098 is not necessary. The main impurity in 50098 is the alcohol 50099 which is formed by hydrolysis of 50095 under the acidic reaction conditions. Elimination of crude 50098 gave 50100 in 80% yield over two steps.

The spiro thiopyran compounds were synthesised by the same route as for the corresponding cyano compounds (see above). Bromohydrine formation with NBS (ref. 12) gave 50115 in 86% yield. Debromination with Bu$_3$SnH (ref. 9) gave the alcohol 50099 in 90% yield. PCC oxidation (ref. 10) of the alcohol gave ketone 50117 in 79% yield. Reaction of the ketone with Lawesson's reagent (ref. 6) gave the thioketone 50120 in quantitative yield as a green solid.

Diels-Alder reaction (ref. 7) with 2,3-dimethyl-1,3-butadiene gave the spiro thiopyran 50121 in 69% yield. NaIO$_4$ oxidation (ref. 3) gave the diastereomeric sulphoxides (ref. 8) 50126 and 50127 in 72% and 14% yield, respectively.

The racemic 7-(2-oxo-pyrrolidinyl) compound 50123 was prepared (yield 42%) by the reaction of the sodium salt of 2-pyrrolidinone with the epoxide formed in situ from bromohydrine 50115.

The optically active compound 50108 was prepared following the same route as for 11903. Asymmetric epoxidation (ref. 15) of 50100 gave at 10:1 mixture of the trans and cis diols 50104 and 50105 in 79% yield. Formation of the epoxide from this diol mixture (MsCl, Et$_3$N, CH$_2$Cl$_2$, 0° C., 10 min) and reaction with an excess of the sodium salt of 2-pyrrolidinone (DMF, r.t.) gave the optical active compound 50108 in 14% yield. The dehydrated product 50109 was isolated in 12% yield.

According to chiral HPLC analysis (column: CHIRACEL OD) the batch of 50108 was a mixture of 50108 (t$_r$=~12.7 min, 91.5%), its enantiomer (t$_r$=~8.2 min, 3.3%, checked with the racemic batch of 50123) and an unknown impurity (t$_r$=~9.0 min, 4.5%). So the optical purity is 93% ee, the compound purity 94.7%.

50012 (Intermediate)

6,7-Dihydro-7-methoxy-5,5-dimethyl-5H-thieno[3,2-b]pyran

A 4 L-round-bottomed flask equipped with a magnetic stirring bar was charged with 40111 (60.0 g, 329 mmol) and 700 ml of MeOH. The flask was placed in an ice bath. To this stirred solution, sodium borohydride (42.0 g, 1.11 mol) was added in small portions (gas evolution!). After the last addition the reaction mixture was stirred for 90 minutes. When the reduction was complete (TLC check), approximately 200 ml of a H$_2$SO$_4$/MeOH solution (32 ml conc H$_2$SO$_4$ in 240 ml of MeOH) was added dropwise (gas evolution!) until pH 2—3 (pH-paper check). The reaction mixture was stirred for 30 minutes. When conversion to the methoxy compound was complete (TLC check), a solution of KOH in MeOH (12.0 g KOH in 200 ml of MeOH) was added until pH 7–8 (pH-paper check). The mixture was poured into 2 L of ice water and extracted with 4×500 ml of CH$_2$Cl$_2$. The collected organic layers were dried (MgSO$_4$) and concentrated in vacuo to give 50012 (63 g, 320 mmol, quantitative yield) as a yellow oil. The oil has a high purity according to $^1$H NMR and TLC.

50095 (Intermediate)

6,7-Dihydro-7-methoxy-5,5-dimethyl-2-(phenylthio)-5H-thieno[3,2-b]pyran 50012 (29.0 g, 146 mmol) was dissolved into 500 ml of THF under a nitrogen atmosphere. The solution was cooled down to −60° C. and at this temperature BuLi (187 ml, 299 mmol, 1.6 M solution in n-hexane) was added dropwise. The reaction mixture became red then dark brown. The reaction mixture was allowed to warm up to −30° C. over a 2 h period. The mixture was placed into an ice bath and the reaction was stirred for 30 min at 0° C. The reaction mixture was cooled down to −60° C. and a solution of diphenyl disulphide (63.8 g, 292 mmol) in 200 ml of THF was added dropwise. The reaction mixture was allowed to warm up to −50° C. over a 1 h period. The mixture was allowed to warm up to room temperature and poured into 2 L of water and extracted (4×) with 500 ml of CH$_2$Cl$_2$. The collected organic layers were washed (2×) with 500 ml of water then dried (K$_2$CO$_3$) and concentrated in vacuo. The residue was purified by chromatography over a 4 L G3 glass filter funnel charged with 1.5 kg of silica gel KG60 and petroleum ether/EtOAc 10/1 as eluant to give 50095 (26.0 g, 84.9 mmol, 58%) as an orange oil.

50098 (Intermediate)

6,7-Dihydro-7-methoxy-5,5-dimethyl-2-(phenylsulphonyl)-5H-thieno[3,2-b]pyran 50095 (30.1 g, 98.2 mmol) was dissolved in 1300 ml of methanol and the solution was placed into an ice bath. At 0°

C., a solution of Oxone® (150.9 g, 245.5 mmol) in 450 ml of water was added dropwise. After the addition the reaction mixture was allowed to warm up to room temperature. After stirring for 3 h the mixture was poured into 2.5 L of ice water and extracted (3×) with 600 ml of $CH_2Cl_2$. The collected organic layers were washed (3×) with 300 ml of water then dried ($MgSO_4$) and concentrated in vacuo to give 34 g of a yellow oil which crystallised on standing. Crystallisation from petroleum ether/EtOAc gave 50098 (26.3 g, 77.7 mmol, 79%) as a light yellow solid.

50099 (Intermediate)

6,7-Dihydro-7-hydroxy-5,5-dimethyl-2-(phenylsulphonyl)-5H-thieno[3,2-b]pyran 50115 (1.05 g, 2.60 mmol) was dissolved in 30 ml of benzene. To the solution AIBN (20 mg, 0.12 mmol) and tributyltin hydride (0.77 ml, 0.83 g, 2.85 mmol) were added and the mixture was heated under reflux. After 3 h, the reaction mixture was allowed to cool down to room temperature and concentrated in vacuo to give a light brown solid. Crystallisation from petroleum ether/EtOAc gave 50099 (0.76 g, 2.34 mmol, 90%) as a white solid.

50100 (Intermediate)

5,5-Dimethyl-2-(phenylsulphonyl)-5H-thieno[3,2-b]pyran 50098 (8.60 g. 25.4 mmol) was dissolved into 380 ml of $CH_2Cl_2$ and molecular sieves 5 Å (46.4 g) was added and the mixture was placed into an ice bath. At 0° C., p-toluenesulfonic acid monohydrate (1.6 g, 8.4 mmol) was added and the mixture was allowed to warm up to room temperature. After 3 h, p-toluenesulfonic acid monohydrate (0.2 g, 1.0 mmol) and molecular sieves 5 Å (5.0 g) were added and the reaction mixture was stirred for 1 h. The molecular sieves were filtered off over celite and the filtrate was washed with 400 ml of a saturated $NaHCO_3$ solution. The organic layer was dried ($MgSO_4$) and concentrated in vacuo to give 7.8 g of a light brown oil. This oil was purified by chromatography over a 1 L G3 glass filter funnel charged with 430 g of silica gel KG60 and petroleum ether/EtOAc 3/1 as eluant to give 50100 (7.0 g, 22.8 mmol, 90%) as a light brown oil.

50101

5,5-Dimethyl-(2,5-dihydro-3,4-dimethyl-thien-2-yl)-5H-thieno[3,2-b]pyran-2-carbonitrile 50096 (0.10 g, 0.31 mmol) was dissolved into acetic anhydride (5 ml) and heated for 3 h at 70° C. The reaction mixture was concentrated in vacuo. Toluene (10 ml) was added to the residue and concentrated in vacuo. The residue was purified by flash chromatography (eluant petroleum ether/EtOAc 30/1) to give 50101 (50 mg, 0.17 mmol, 55%) as a yellow wax. $^1$H NMR (400 MHz, $CDCl_3$) 1.44 (s, 3 H), 1.49 (s, 3 H), 1.57 (bs, 3 H), 1.76 (bs, 3 H), 3.79 (bd, J=15.2 Hz, 1 H), 3.82 (bd, J=15.2 Hz, 1 H), 4.77 (bs, 1H), 5.39 (s, 1 H), 7.03 (s, 1 H). $^{13}$C NMR (100 MHz, $CDCl_3$) 13.1, 15.2, 27.1, 27.6, 43.5, 62.0, 79.4, 106.5, 115.1, 118.8, 126.0, 126.4, 129.6, 130.5, 134.3, 152.3.

50104 and 50105 (Intermediates)

(?)-(6S,7S)-6,7-Dihydro-6,7-hydroxy-5,5-dimethyl-2-(phenylsulphonyl)-5H-thieno[3,2-b]pyran (50104)

(?)-(6S,7R)-6,7-Dihydro-6,7-hydroxy-5,5-dimethyl-2-(phenylsulphonyl)-5H-thieno(3,2-b]pyran (50105)

A mixture of 15 ml NaOCl solution (ca. 12–13% Cl active, Riedel-de Haën), 36 ml of water and 20 ml of a $Na_2HPO_4$ was prepared with pH 11.3. The mixture was placed into an ice bath. To this Stirred mixture a solution of 50100 (2.0 g, 6.5 mmol), Mn(III) salen epoxidation catalyst (0.3 g, 0.47 mmol) and 4-phenylpyridine-N-oxide (0.4 g, 2.3 mmol) in 100 ml of $CH_2Cl_2$ was added dropwise. This epoxidation catalyst is available from Aldrich. The reaction mixture was stirred vigorously at 0° C. for 1 h. The organic layer was separated and the water layer extracted (3×) with 100 ml of $CH_2Cl_2$. The collected organic layers were filtered over celite and then washed (2×) with water. The organic layer was concentrated in vacuo. The residue was dissolved into a mixture of 30 ml of acetone, 5 ml of water and 1 ml of concentrated sulfuric acid. The mixture was stirred for 1 h at room temperature. The mixture was dissolved into 300 ml of $CH_2Cl_2$ and washed with a saturated $NaHCO_3$ solution. The organic layer was dried ($MgSO_4$) and concentrated in vacuo to give 2.8 g of a brown oil. This oil was purified by flash chromatography (eluant petroleum ether/EtOAc 1/1) to give a 10:1 mixture of the trans and cis diols 50104 and 50105 (1.75 g, 5.14 mmol, 79%) as a light brown oil.

50106

5,5-Dimethyl-(2,5-dihydro-3,4-dimethyl-1-oxy-thien-2-yl)-5H-thieno[3,2-b]pyran-2-carbonitrile 50101 (50 mg, 0.17 mmol) was dissolved into a mixture of methanol (10 ml) and isopropanol (5 ml) and placed in an ice bath. At 0° C. a solution of sodium periodate (40 mg, 0.19 mmol) in water (2 ml) was added dropwise. After stirring for 6 h a solution of sodium periodate (20 mg, 0.09 mmol) in water (1 ml) was added dropwise and the reaction mixture was allowed to warm up to room temperature and stirred overnight. The white precipitation was filtered off and the filtrate was taken up in ethyl acetate (100 ml). The organic layer was washed with water (30 ml). The organic layer was dried ($MgSO_4$) and concentrated in vacuo. The residual oil was purified by flash chromatography (eluant: EtOAc) to give 50106 (40 mg, 0.13 mmol, 76%) as white crystals. Mp. 154–161° C. $^1$H NMR (400 MHz, $CDCl_3$) 1.44 (s, 3 H), 1.52 (s, 3 H), 1.71 (s, 3 H), 1.90 (s, 3 H), 3.46 (bd, J=16.6 Hz, 1 H), 4.00 (bd, J=16.8 Hz, 1 H), 4.32 (bs, 1 H), 5.43 (s, 1 H), 7.08 (t, 1H). $^{13}$C NMR (100 MHz, $CDCl_3$) 13.6, 15.3, 27.1, 27.5, 63.2, 79.8, 83.0, 106.7, 114.2, 119.7, 123.5, 127.3 (2×C), 128.4, 131.7, 152.0.

50108 and 50109

(?)-(6S, 7S)-6,7-Dihydro-6-hydroxy-5,5-dimethyl-7-(2-oxo-1-pyrrolidinyl)-2-(phenylsulphonyl)-5H-thieno[3,2-b]pyran (50108)

5,5-Dimethyl-7-(2-oxo-1-pyrrolidinyl)-2-(phenylsulphonyl)-5H-thieno[3,2-b]pyran (50109)

Sodium Salt of 2-pyrrolidinone

A 60–65% dispersion of NaH (0.60 g, 14.4 mmol) in mineral oil was washed (3×) with petroleum ether under a nitrogen atmosphere and then 50 ml of DMF was added. To the suspension 2-pyrrolidinone (1.1 ml, 1.2 g, 14.4 mmol, water azeotropicly removed with toluene) was added dropwise (Caution: foam formation). The mixture was allowed to warm up to room temperature and stirred for 30 min.

Epoxide Formation

The 50104/50105 mixture (1.6 g, 4.8 mmol, vide supra) was dissolved into 70 ml of $CH_2Cl_2$ under a nitrogen atmosphere and placed into an ice bath. At 0° C., triethylamine (1.5 ml, 1.1 g 10.6 mmol) and mesyl chloride (0.4 ml, 0.6 g, 5.0 mmol) were added, subsequently. The reaction mixture was stirred for 10 min then poured into 200 ml of ice water and extracted with $CH_2Cl_2$. The collected organic layers were dried ($MgSO_4$) and concentrated in vacuo.
Reaction of the Epoxide with the Sodium Salt of 2-pyrrolidinone The crude epoxide was dissolved into 20 ml of DMF and added to the solution of the sodium salt of 2-pyrrolidinone at room temperature. The reaction mixture became dark red. The mixture was stirred for 4 h at room temperature and then poured into 1 L of ice water. The water layer was neutralized by adding a 10% $H_2SO_4$ solution. The water layer was extracted (6×) with 200 ml of EtOAc. The collected organic layers were washed (2×) with 300 ml of water. The organic layer was dried ($MgSO_4$) and concentrated in vacuo to give 2.5 g of a dark brown oil. The oil was purified by flash chromatography (eluant: EtOAc) to give 50108 (0.28 g, 0.69 mmol, 14%, light yellow solid) and 50109 (0.23 g, 0.59 mmol, 12%, light brown oil).

50108: According to chiral HPLC analysis (column: CHIRACEL OD; flow: 1 ml/min; wavelength: 230 nm; mobile phase: n-heptane/n-propanol/triethylamine 80/20/0.05; column temp: 40° C.; Inj. vol: 10 ml) [4413020] it was a mixture of 50108 ($t_r$=~12.7 min, 91.5%) its enantiomer ($t_r$=~8.2 min, 3.3%) and an unknown impurity ($t_r$=~9.0 min, 4.5%). Optical purity: 93% ee, chemical purity 94.7%. $R_f$=0.32 (EtOAc). $^1$H NMR (400 MHz, DMSO-d6) 1.17 (s, 3 H), 1.39 (s, 3 H), 1.85–2.05 (m, 2 H), 2.33 (t, J=7.9 Hz, 2 H), 3.05–3.15 (m, 1 H), 3.30–3.45 (m, 1 H), 3.74 (dd, J=9.6, 6.0 Hz, 1 H), 4.94 (d, J=9.6 Hz, 1 H), 5.78 (d, J=6.0 Hz, 1 H), 7.42 (s, 1 H), 7.60–7.75 (m, 3 H), 7.94–8.00 (m, 2 H). $^{13}$C NMR (100 MHz, DMSO-d6) 18.0, 18.1, 26.5, 30.7, 42.5, 50.3, 69.0, 81.6, 121.3, 124.8, 127.1, 129.9, 134.1, 139.2, 141.3, 151.0, 175.4.

50109: $R_f$=0.53 (EtOAc). $^1$H NMR (400 MHz, CDCl$_3$) 1.47 (s, 6 H), 2.05–2.20 (m, 2 H), 2.51 (t, J=7.0 Hz, 2 H), 3.65 (t, J=7.0 Hz, 2 H), 5.27 (s, 1 H), 7.13 (s, 1 H), 7.45–7.60 (m, 3 H), 7.95–8.00 (m, 2 H). $^{13}$C NMR (100 MHz, CDCl$_3$) 18.8, 27.6, 31.6, 49.5, 79.9, 118.9, 120.3, 122.9, 127.3, 129.1, 129.3, 133.3, 139.6, 141.9, 152.5, 174.6.

50110 and 50111

3',6,6',7-Tetrahydro-4',5,5,5'-tetramethyl-spiro[5H-thieno[3,2-b]pyran-7,2'-2H-thiopyran]-1',1'-dioxide (50110) and 4',5'-Epoxy-3',6,6',7-tetrahydro-4',5,5,5'-tetramethyl-spiro[5H-thieno[3,2-b]pyran-7,2'-2H-thiopyran]-1',1'-dioxide (50111)

50049 (138.0 mg, 0.492 mmol) was dissolved into a mixture of isopropanol (3 ml) and methanol (2 ml). At r.t. a solution of oxone (0.85 g) was added dropwise and the reaction mixture was stirred overnight, The reaction mixture was poured into water (15 ml) and extracted (3×15 ml) with dichloromethane. The collected organic layers were dried ($MgSO_4$) and concentrated in vacuo. The residual oil was purified by flash chromatography (eluant: petroleum ether/EtOAc 2/1) to give 50110 (25 mg, 0.08 mml, 16%, light yellow oil) and 50111 (20 mg, 0.06 mmol, 12%, light yellow oil) and a 1:1 mixed fraction (60 mg, 38%) of 50110 and 50111

50110: $^1$H NMR (400 MHz, CDCl$_3$) 1.34 (s, 3H), 1.51 (s, 3 H), 1.71 (s, 3 H), 1.77 (s, 3 H), 1.98 (d, J=14.2 Hz, 1 H), 2.68 (d, J=14.2 Hz, 1 H), 2.90 (bd, J=17.8 Hz, 1 H), 3.00 (bd, J=17.8 Hz, 1 H), 3.63 (bd, J=17.7 Hz, 1 H), 3.70 (bd, J=17.7 Hz, 1 H), 6.62 (d, J=5.5 Hz, 1 H), 7.19 (d, J=5.5 Hz, 1 H). $^{13}$C NMR (100 MHz, CDCl$_3$) 19.7, 20.0, 26.3, 29.4, 38.4, 46.8, 53.0, 59.6, 76.0, 105.4, 119.3, 120.3, 125.7, 126.3, 154.4.

50111: $^1$H NMR (400 MHz, CDCl$_3$) 1.37 (s, 6H), 1.47 (s, 3 H), 1.51 (s, 3 H), 2.47 (d, J=14.2 Hz, 1 H), 2.68 (d, J=14.2 Hz, 1 H), 2.86 (bd, J=16.0 Hz, 1 H), 2.92 (bd, J=16.0 Hz, 1 H), 3.28 (bd, J=15.7 Hz, 1 H), 3.70 (bd, J=15.7 Hz, 1 H), 6.61 (d, J=5.5 Hz, 1 H), 7.23 (d, J=5.5 Hz, 1 H). $^{13}$C NMR (100 MHz, CDCl$_3$) 20.5, 22.1, 25.6, 29.7, 38.6, 43.5, 53.4, 59.3, 60.9, 61.9, 76.2, 104.2, 119.3, 126.2, 155.1.

50115 (Intermediate)

rel-(6R, 7R)-6 Bromo-6,7-dihydro-7-hydroxy-5,5-dimethyl-2-(phenylsulphonyl)-5H-thieno[3,2-b]pyran (50115)

50100 (1.96 g, 6.34 mmol) was dissolved in 70 ml of DMSO and water (0.18 ml, 10 mmol) was added. At room temperature, NBS (1.20 g, 6.74 mmol) was added. The reaction mixture became light brown. The mixture was stirred for 2 h then poured into water and extracted (2×) with EtOAc. The collected organic layers were washed with water then dried ($MgSO_4$) and concentrated in vacuo to give a brown solid. Crystallisation from petroleum ether/EtOAc gave 50115 (2.21 g, 5.48 mmol, 86%) as a light brown solid. $R_f$=0.33 (petroleum ether/EtOAc 3/1).

50117 (Intermediate)

6,7-Dihydro-5,5-dimethyl-7-oxo-2-(phenylsulphonyl)-5H-thieno[3,2-b]pyran (50117)

Under a $N_2$ atmosphere, PCC (0.65 g, 3.0 mmol) was suspended in 30 ml of $CH_2Cl_2$ and a solution of 50099 (650 mg, 2.00 mmol) in 20 ml of $CH_2Cl_2$ was added. The orange suspension turned black. After stirring for 1 h, 100 ml of diethyl ether was added and the mixture was filtered off over celite. Activated charcoal was added and the mixture was filtered off and concentrated in vacuo to give a light brown solid. The solid was purified by flash chromatography (eluant: petroleum ether/EtOAc 2/1) to give 50117 (510 mg, 1.58 mmol, 79%) as a white solid.

50120 (Intermediate)

6,7-Dihydro-5,5-dimethyl-7-thio-2-(phenylsulphonyl)-5H-thieno[3,2-b]pyran 50117 (0.50 g, 1.55 mmol) was dissolved in 30 ml of toluene and Lawesson's reagent (0.54 g, 1.34 mmol) was added portionwise over a 90 min period to the mixture, heated under reflux. The reaction mixture was allowed to cool down to room temperature and concentrated in vacuo. The residue was purified by flash chromatography (eluant: petroleum ether/EtOAc 2/1) to give 50120 (0.54 g, 1.59 mmol, quantitative yield) as a green wax.

50121

3',6,6',7-Tetrahydro-4',5,5,5'-tetramethyl-2-(phenylsulphonyl)spiro[5H-thieno[3,2-b]pyran-7,2'-2H-thiopyran]

A 135 cm$^3$ autoclave was charged with a solution of 50120 (0.50 g, 1.48 mmol) in 30 ml of toluene. To the solution 2,3-dimethyl-1,3-butadiene (0.29 ml, 0.20 g, 2.96 mmol) was added. The autoclave was closed and heated at 130° C. for 18 h. The reaction mixture was allowed to cool down to room temperature and concentrated in vacuo to give 0.73 g of an orange solid. Crystallisation from EtOAc gave 0.30 g of 50121 as a light yellow solid. The mother liquor was concentrated in vacuo and the residue was purified by flash chromatography (eluant: petroleum ether/EtOAc 5/1) to give a subsequent 0.13 g of 50121. Total yield: 0.43 g, 1.02 mmol, 69%. Mp: 175–178° C. $R_f$=0.37 (petroleum ether/EtOAc 4/1). $^1$H NMR (400 MHz, CDCl$_3$) 1.38 (s, 3 H), 1.47 (s, 3 H), 1.68 (s, 3 H), 1.83 (s, 3 H), 2.00 (d, J=14.7 Hz, 1 H), 2.15 (d, J=14.7 Hz, 1 H) 2.26 (bd, J=17.0 Hz, 1 H), 2.51 (bd, J=17.0 Hz, 1 H), 3.15 (d, J=17.5 Hz, 1 H), 3.35 (d, J=17.5 Hz, 1 H), 7.11 (s, 1 H), 7.45–7.60 (m, 3 H), 7.95–8.00 (m, 2 H). $^{13}$C NMR (100 MHz, CDCl$_3$) 19.2, 20.8, 26.8, 29.7, 31.7, 39.4, 47.1, 48.2, 77.2, 124.3, 126.2, 127.4, 127.6, 129.2, 133.2, 138.6, 142.1, 149.7.
50123 rel-(6S,7S)-6,7-Dihydro-6-hydroxy-5,5-dimethyl-7-(2-oxo-1-pyrrolidinyl)-2-(phenylsulphonyl)-5H-thieno[3,2-b]pyran A 60–65% dispersion of NaH (0.30 g, 7.44 mmol) in mineral oil was washed with petroleum ether under a nitrogen atmosphere and then 50 ml of DMSO was added. To the suspension 2-pyrrolidinone (0.57 ml, 0.62 g, 7.44 mmol, water azeotropicaly removed with toluene) was added dropwise and stirred for 30 min. To this mixture a solution of 50115 (0.50 g, 1.24 mmol) in 15 ml of DMSO was added dropwise. The reaction mixture turned dark brown and was stirred for 1 h. The mixture was poured into 400 ml of ice water and extracted (4×) with 200 ml of ether. The combined organic layers were washed with 200 ml of water then dried (MgSO$_4$) and concentrated in vacuo. The residue was purified by flash chromatography (eluant: EtOAc) to give 50123 (214 mg, 0.525 mmol, 42%) as a light yellow foam. According to chiral HPLC analysis (column: CHIRACEL OD; flow: 1 ml/min; wavelength: 230 nm; mobile phase: n-heptane/n-propanol/triethylamine 80/20/0.05; column temp: 40° C.; Inj. vol: 10 ml) [4417037] this compound was a 1:1 mixture of 50108 ($t_r$=~12.7 min) its enantiomer ($t_r$=~7.9 min). Chemical purity: 96%. $R_f$=0.31 (EtOAc). $^1$H NMR (400 MHz, CDCl$_3$) 1.27 (s, 3 H), 1.47 (s, 3 H), 2.05–2.20 (m, 2 H), 2.51 (t, J=8.0 Hz, 2 H), 3.25–3.40 (m, 2 H), 3.76 (d, J=9.6 Hz, 1 H), 5.26 (d, J=9.2 Hz, 1 H), 7.13 (s, 1 H), 7.50–7.65 (m, 3 H), 7.95–8.00 (m, 2 H).
50126 and 50127 rel-(1'R,2'R)-3',6,6',7-Tetrahydro-4',5,5',5-tetramethyl-2-(phenylsulphonyl)spiro[5H-thieno[3,2-b]pyran-7,2'-2H-thiopyran]1'-oxide (50126)

rel-(1'R,2'S)-3',6,6',7-Tetrahydro-4',5,5',5-tetramethyl-2-(phenylsulphonyl)spiro[5H-thieno[3,2-b]pyran-7,2'-2H-thiopyran]1'-oxide (50127)

50121 (0.27 g, 0.64 mmol) was dissolved in a mixture of 360 ml of methanol and 180 ml of isopropanol. The mixture was placed in an ice bath and at 0° C. a solution of NaIO$_4$ (0.16 g, 0.64 mmol) in 15 ml of water was added. The reaction mixture was allowed to warm up to room temperature. The reaction mixture became turbid. The mixture was stirred overnight. A solution of NaIO$_4$ (0.16 g, 0.64 mmol) in 15 ml of water was added and stirred overnight. The white precipitation was filtered off and the filtrate was dissolved into 300 ml of CH$_2$Cl$_2$. The a organic layer was washed (3×) with 300 ml of water then dried (MgSO$_4$) and concentrated in vacuo to give 0.39 g of a light yellow solid. The residue was purified by flash chromatography (eluant: EtOAc) to give 50126 (0.20 g, 0.46 mmol, 72%) as a light yellow solid and 50127 (0.04 g, 0.092 mmol, 14%) as a light yellow oil and starting material (0.06 g, 0.14 mmol, 14%).

50126: $R_f$=0.43 (EtOAc). $^1$H NMR (400 MHz, CDCl$_3$) 1.42 (s, 3 H), 1.50 (s, 3 H), 1.64 (d, J=15.2 Hz, 1 H), 1.74 (s, 3 H), 1.83 (s, 3 H), 1.94 (d, J=17.6 Hz, 1 H), 2.63 (d, J=15.2 Hz, 1 H), 2.99 (d, J=17.6 Hz, 1 H), 3.24 (d, J=18.4 Hz, 1 H), 3.64 (d, J=18.4 Hz, 1 H), 7.10 (s, 1 H), 7.45–7.60 (m, 3 H), 7.95–8.00 (m, 2 H). $^{13}$C NMR (100 MHz, CDCl$_3$) 19.4, 20.5, 26.4, 29.7, 37.8, 38.5, 49.6, 53.9, 77.3, 117.4, 118.7, 124.4, 126.7, 127.5, 129.4, 133.5, 141.5, 153.8.

50127: $R_f$=0.54 (EtOAc). $^1$H NMR (400 MHz, CDCl$_3$) 1.42 (s, 3 H), 1.50 (s, 3 H), 1.70 (d, J=14.5 Hz, 1 H), 1.72 (s, 3 H), 1.76 (s, 3 H), 1.92 (d, J=14.5 Hz, 1 H), 2.25 (d, J=17.6 Hz, 1 H), 3.13 (d, J=17.6 Hz, 1 H), 3.22 (d, J=18.3 Hz, 1 H), 3.31 (d, J=18.3 Hz, 1 H), 7.19 (s, 1 H), 7.45–7.60 (m, 3 H), 7.95–8.00 (m, 2 H). $^{13}$C NMR (100 MHz, CDCl$_3$) 19.2, 20.4, 26.9, 28.9, 36.7, 38.3, 49.1, 53.4, 76.5, 115.6, 121.5, 123.7, 125.7, 127.6, 129.3, 133.3, 141.6, 141.7, 151.3.
50133

5,5-Dimethyl-7-(2-oxo-1-pyrrolidinyl)-2-(thiazolin-2-yl)-5-thieno[3,2-b]pyran 50040 (226.3 mg, 0.825 mmol) was dissolved in dichloromethane (6 ml) and cysteamine (169.3 mg, 2.20 mmol) and a few crystals of pyridinium p-toluenesulfonate were added. The reaction mixture was refluxed overnight. The mixture was taken up in 30 ml of dichloromethane and washed with water. The organic fraction was dried (MgSO$_4$) and concentrated in vacuo. The residual oil was purified by flash chromatography (eluant: EtOAc) to give 50133 (262.6 mg, 0.785 mmol, 95%) as an orange oil. $^1$H NMR (400 MHz, CDCl$_3$) 1.43 (s, 6 H), 2.04 (quintet, J=7.8 Hz, 2 H), 2.43 (t, J=7.8 Hz, 2 H), 3.34 (t, J=8.2 Hz, 2 H), 3.64 (t, J=7.8 Hz, 2 H), 4.28 (t, J=8.2 Hz, 2 H), 5.33 (s, 1 H), 6.87 (s, 1 H). $^{13}$C NMR (100 MHz, CDCl$_3$) 18.8, 27.4 (2×C), 31.6, 34.5, 49.4, 64.6, 79.8, 115.6, 119.4, 121.1, 128.9, 133.4, 152.9, 161.5, 174.6.
50203 and 50204

3',4',5',6,6',7-Hexahydro-5,5-dimethyl-5'-oxo-2-(phenylsulphonyl)-spiro[5-thieno[3,2-b]pyran-7,2'-2H-thiopyran] (50203)

3',4',5',6,6',7-Hexahydro-5,5-dimethyl-4'-oxo-2-(phenylsulphonyl)-spiro[5H-thieno[3,2-b]pyran-7,2'-2H-thiopyran] (50204)

A 135 cm$^3$ autoclave was charged with a solution of 50120 (173 mg, 0.511 mmol) in 20 ml of toluene. To the solution was added 2-(trimethlsilyloxy)-1,3-butadiene (0.45 g, 3.16 mmol). The autoclave was closed and heated at 130° C. for 16 h. The reaction mixture was allowed to cool to room temperature and concentrated in vacuo. The residual oil was purified by flash chromatography (eluant: petroleum ether/EtOAc 1/1) to give 50203 (44 mg, 0.11 mmol, 21%, yellow oil/wax) and 50204 (20 mg, 0.05 mmol, 10%, yellow oil).

50203: $^1$H NMR (400 MHz, CDCl$_3$) 1.47 (s, 3 H), 1.50 (s, 3 H), 2.20 (d, J=14.5 Hz, 1 H), 2.35–2.45 (m, 1 H), 2.55–2.75 (m, 3 H), 2.59 (d, J=14.5 Hz, 1 H), 3.35 (d, J=14.3 Hz, 1 H), 3.46 (d, J=14.3 Hz, 1 H), 7.16 (s, 1 H), 7.50–7.70 (m, 3 H), 7.95–8.05 (m, 2 H)).

50204: $^1$H NMR (400 MHz, CDCl$_3$) 1.39 (s, 3 H), 1.46 (s, 3 H), 2.00 (d, J=14.7 Hz, 1 H), 2.24 (d, J=14.7 Hz, 1 H), 2.70–2.85 (m, 2 H), 2.75 (d, J=13.0 Hz, 1 H), 3.03 (d, J=13.0 Hz, 1 H), 3.05–3.20 (m, 2 H), 7.15 (s, 1 H), 7.55–7.70 (m, 3 H), 7.95–8.05 (m, 2 H).

50113, 50119, 50134, 50135 and 50174 (All Intermediates) and 50174

2-Trifluoroacetyl-6, 7-dihydro-7-methoxy-5,5-dimethyl-5H-thieno[3,2-b]pyran (50113)

Under a nitrogen atmosphere, 6,7-dihydro-7-methoxy-5, 5-dimethyl-5H-thieno[3,2-b]pyran 50012 (1.31 g, 6.61 mmol) was dissolved into THF (70 ml). The reaction mixture was placed into a EtOH/CO$_2$ bath of −60° C. At this temperature a solution of BuLi (8.5 ml, 1.6 M in hexane) was added dropwise. The mixture was allowed to warm up to −20° C. over a 1.5 h period. The mixture was placed into an ice bath and stirred for 30 min at this temperature. The mixture was placed into a EtOH/CO$_2$ bath of −30° C. and magnesium bromide etherate (3.42 g, 13.2 mmol) was added portionwise. Slowly the salt dissolved into the mixture and the mixture became turbid, After stirring for 45 min the mixture was cooled down to −60° C. and trifluoro acetic anhydride (1.90 ml, 13.7 mmol) was added dropwise. The mixture became yellow then brown again. The mixture was allowed to warm up to room temperature. The mixture was taken up into dichloromethane and washed with a half saturated sodium bicarbonate solution. The water layer was extracted (2×) with dichloromethane. The collected organic layers were dried (MgSO$_4$) and concentrated in vacuo to give a brown oil (2.39 g). The oil was purified by flash chromatography (eluant: petroleum ether/EtOAc 6/1) to give 50113 (1.39 g, 4.72 mmol, 71%) as a brown oil.

2-Trifluoroacetyl-5,5-dimethyl-5H-thieno[3,2-b]pyran (50119)

To a solution of 50113 (11.12 g, 37.8 mmol) in dichloromethane (500 ml) at 0° C., were added molecular sieves 5 Å (65 g) and benzenesulphonic acid (1.50 g, 9.48 mmol). After 10 min the mixture was allowed to warm to room temperature. After stirring for 4 h, a second portion of molecular sieves 5 Å (25 g) and benzenesulphonic acid (0.80 g, 5.1 mmol) were added. After 1 h the reaction mixture was filtered off over celite and the filtrate was washed with a saturated bicarbonate solution. The organic layer was dried (K$_2$CO$_3$) and concentrated in vacuo (the compound is very volatile) to give a dark brown oil (8.98 g). The oil was purified by chromatography over a 1 L G3 glass filter funnel charged with 400 g of silica gel KG60 and petroleum ether/EtOAc 5/1 as eluant to give 50119 (7.64 g, 29.1 mmol, 77%) as a brown oil.

2-(Pentafluoroethyl)-5,5-dimethyl-5H-thieno[3,2-b]pyran (50134)

Under a nitrogen atmosphere, a solution of 50119 (530 mg, 2.02 mmol) in dichloromethane (5 ml) was placed into an ice bath, To the solution, diethylaminosulphur trifluoride (0.40 ml, 3.0 mmol) was added. After 10 min the reaction mixture was allowed to warm to room temperature and stirred for 18 h. The reaction mixture was poured into water and extracted with dichloromethane. The collected organic layers were dried (MgSO$_4$) and concentrated in vacuo (the compound is very volatile). The oil was purified by flash chromatography (eluent petroleum ether 40/50) to give 50134 (330 mg, 1.16 mmol, 57%) as a colorless oil. R$_f$=0.72 (hexane).

rel-(6R, 7R)-6 Bromo-2-(pentafluoroethyl)-6,7-dihydro-7-hydroxy-5,5-dimethyl-5H-thieno[3,2-b] pyran (50135)

50134 (330 mg, 1.16 mmol) was dissolved in DMSO (5 ml) and water (0.05 ml, 2.8 mmol) was added. The mixture was stirred at room temperature and NBS (230 mg, 1.29 mmol) was added. After stirring for 2 h, the mixture was poured into water (200 ml) and extracted (2×100 ml) with ethyl acetate. The collected organic layers were washed with brine (100 ml) then dried (MgSO$_4$) and concentrated in vacuo to give a yellow oil. The oil was purified by flash chromatography (eluant: petroleum ether/EtOAc 3/1) to give 50135 (357.2 mg, 0.984 mmol, 85%) as a yellow oil.

rel-(6S, 78S)-2-(Pentafluoroethyl)-6,7-dihydro-6-hydroxy-5,5-dimethyl-7-(2-oxo-1-piperidinyl)-5H-thieno[3,2-b]pyran (50174)

Sodium hydride (0.28 g, 6.42 mmol, 60–65% in oil) was a washed (2×5 ml) with hexane under a nitrogen atmosphere. The hydride was suspended into DMSO (10 ml) and 2-piperidone (0.62 g, 6.25 mmol) was added dropwise. The mixture became turbid and foamed and was stirred for 30 min. A solution of 50135 (0.62 g, 1.57 mmol) in DMSO (10 ml) was added dropwise. After 30 minutes the reaction mixture was poured into water (300 ml) and extracted with ethyl acetate (5×100 ml). The collected organic fractions were washed with water (100 ml) then dried (MgSO$_4$) and concentrated in vacuo. The residual brown wax was purified by flash chromatography (eluant: EtoAc) to give 50174 (0.20 g, 0.5 mmol, 32%) as red/brown crystals. Mp: 177–178° C. $^1$H NMR (400 MHz, CDCl$_3$) 1.31 (s, 3 H), 1.49 (s, 3 H), 1,75–1.95 (m, 4 H), 2.50–2.55 (m, 2 H), 3.10–3.30 (m, 2 H), 3.52 (bs, 1 H), 3.81 (d, J=9.4 Hz, 1 H), 5.88 (dt, J=9.4, 2.0 Hz, 1 H), 6.92 (s, 1 H). $^{13}$C NMR (100 MHz, CDCl$_3$) 17.8, 20.9, 23.1, 26.3, 32.4, 43.0, 52.8, 72.3, 81.8, 112.2 (tq, $^1J_{C,F}$=253.6 Hz, $^2J_{C,F}$=39.2 Hz), 115.0, 118.7 (qt, $^1J_{C,F}$=282.7 Hz, $^2J_{C,F}$=39.2 Hz), 121.9 (t, $^3J_{C,F}$=5.0 Hz), 127.6 (t, $^2J_{C,F}$=28.2 Hz), 152.4, 173.5.

Cell Growth Potentiation Test

To test for activity in mammalian hair growth stimulation, an in vitro test of cell growth potentiation has been applied to a number of the compounds of the invention and prior art compounds 11901 and 11903. The test involves an assay of the call growth due to potentiation of the mitogenic activity of fetal calf serum (FCS). See WO97/14036. Details of materials, methods and results are as follows.

(i) Materials

Tissue culture plastics were obtained from Beckton Dickinson (Cowley, Oxford, UK). NIH 3T3 fibroblasts were obtained from the European collection of animal cell cultures (Salisbury, Wilts, UK). Dulbecco's modified Eagle's medium (DMEM) was obtained from Flow Laboratories (Rickmansworth, Herts, UK). L-Glutamine and fetal calf serum were from Gibco (Paisley, UK).

The EZ4U cell proliferation assay kits were obtained from Cozart Bioscience Ltd (Abingdon, Oxon, UK). All other chemicals were obtained from Sigma Chemical Company Ltd. (Poole, Dorset, UK), and of the highest grade available.

(ii) Cell Culture

NIH 3T3 fibroblasts were maintained in Dulbecco's modified Eagle's medium supplemented with 10% FCS and 2 mM L-glutamine in 150 $cm^2$ tissue culture flasks at 37° C. in an atmosphere of 5% $CO_2$/95% air. Antibiotics were omitted. Medium was changed every 3 days, and passages were carried out twice a week before cells reached confluence. Prior to experiments, cells were passaged and plated out to give $10^4$ cell/ml in 96-well multi-well plates. Cells were incubated for 24 hours with Dulbecco's modified Eagle's medium supplemented with 10% FCS to aid attachment. This was then removed and the experimental medium added.

(iii) Typical Compound Preparation Protocol

Compounds were prepared following a general preparation protocol. This protocol consisted of taking a mass of compound, dissolving in the recommended solvent (40 μl) such that in the final preparation the concentrations of compound and solvent would be 100 μM and 0.1 respectively. In theory this volume was 40 μl, however for accuracy a mass larger than the required mass was dispensed and the solvent volume varied accordingly; only 40 μl of this solution was required for the next stage. The 40 μl volume was then added to a volume of FCS (1.2 ml), such that in the final preparation the concentration of FCS would be 3%. This solution was then added to DMEM containing L-glutamine (2 mM) (18.76 ml). The resulting solution of 20 ml volume was filter stabilised. This solution is now 200 μM in compound, 6% FCS and 0.2% solvent, and so was diluted 1:1 with the DMEM containing L-glutamine. This 100 μM stock could then be diluted serially to provide lower concentrations of the compound of interest. Solutions containing different ratios of compound and FCS were obtained in a similar manner.

(iv) Cellular Proliferation Assay

This was performed, following the manufacturer's instructions, using an EZ4U assay kit, which is based upon the conversion of tetrazolium salt to coloured formazam derivatives by mitochondria (Hansen et al, 1989). Plates were read on a plate reader (Anthos Labtec HT2), using a measurement filter (450 nm), with a reference filter (620 nm) with a low Shaking density for 5 seconds prior to measurement. Control experiments were made against counting cells in a haemocytometer (sanders et al, 1996). There is some variance of results between different batches of FCS employed.

(v) Results of Tests

Figure 2:
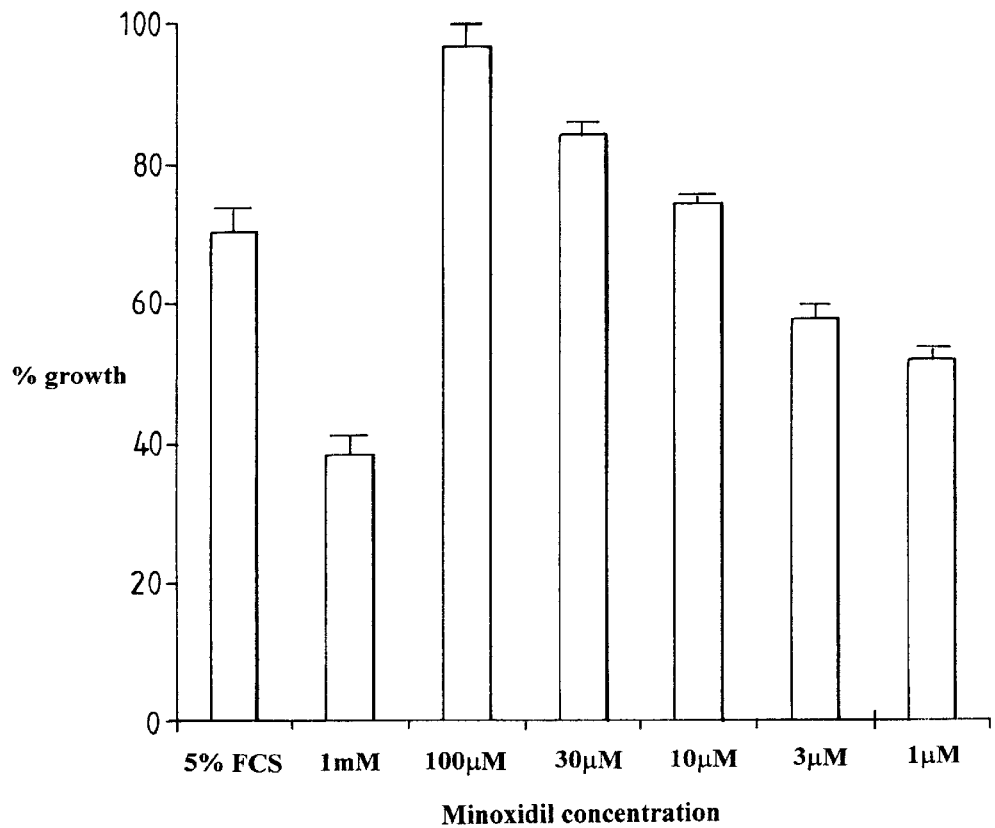
FIG. 2 is a bar chart showing minoxidil potentiation of mitogenic activity in a cell growth test described below.

First, FIG. 2 shows the dose dependency of minoxidil potentiation of mitogenic activity of 5% FCS (in FIG. 2 100% growth is the value for 10% FCS). The greatest effect shown by minoxidil is at 100 μM.

A series of cell growth potentiation/inhibition tests has been carried out in accordance with the procedure described above on some of the compounds of the invention, on compounds 11901 and 11903 and on minoxidil (a compound well known for its hair growth stimulation effects). Because of some variability of results with different batches of FCS, each compound was tested in a solution of a base concentration of FCS and was compared with minoxidil in a solution of the same base concentration of FCS and with a solution having the same base concentration of FCS alone (no additive), using the same FCS batch in order to provide standardised comparisons for that compound. In most cases the base concentration of FCS was 5% but in some cases was 3% when the FCS was particularly potent.

Table 2 gives results of these tests in comparison with the cell growth potentiation arising with minoxidil at 100 μM, taking as a base value (0%) the cell growth occurring in the solution of the base concentration of FCS alone (FCS with no additive compound). The compounds were tested at concentrations of 100 μM and 10 μM, but all results are given as a percentage relative to the potentiation effect of minoxidil at 100 μM. Thus a value of 100% indicates that the compound provided the same cell growth as minoxidil at 100 μM, while a value of 0% indicates that with the compound the cell growth was the same as for a solution of the base concentration of FCS alone.

TABLE 2

| Compound | Cell growth potentiation relative to minoxidil at 100 μM (%) | |
|---|---|---|
| | Compound at 100 μM | Compound at 10 μM |
| 11901 | 28 | 0 |
| 11903 | see table 3 | 16 |
| 50040 | 48 | 24 |
| 50057 | 33 | see table 3 |
| 50066 | 144 | 355 |
| 50092 | 71 | 214 |
| 50097 | 257 | 242 |
| 50106 | 60 | see table 3 |
| 50109 | 122 | 233 |
| 50121 | 271 | 285 |
| 50123 | see table 3 | 120 |
| 50133 | see table 3 | 54 |
| 50174 | 133 | 244 |

Table 3 gives results for tests in comparison with the cell growth arising with the base concentration of FCS alone (no additive compound), as a percentage of the value for the solution having the base concentration of FCS alone. Thus a 100% value indicates that the same cell growth occurred with the compound present as in the solution having the base concentration of FCS alone.

TABLE 3

| Compound | Cell growth relative to FCS alone (%) | |
|---|---|---|
| | Compound at 100 μM | Compound at 10 μM |
| 11903 | 89 | see table 2 |
| 50049 | 50 | 100 |
| 50057 | see table 2 | 98 |
| 50063 | 93 | 55 |
| 50067 | 69 | 96 |
| 50070 | 78 | 81 |
| 50106 | see table 2 | 80 |
| 50123 | 94 | see table 2 |
| 50133 | 60 | see table 2 |

The results in Tables 2 and 3 show that compounds of the invention have significant effects in modulation of cell growth rates, in a test which is believed to be indicative of activity in control of mammalian hair growth. Some compounds (Table 2) show substantial stimulation of cell growth, even at 10 μM concentration, which is believed to be a concentration level comparable to that obtainable in vivo. In some cases, the potentiation effect is much greater than that of minoxidil. Other compounds (Table 3) show inhibition of cell growth, which is indicative of the pharmaceutically and cosmetically useful property of inhibition of hair growth.

REFERENCES

1. Kumar, V.; Dev, S. Tetrahedron Lett. 1983, 24, 1289.
2. For reactions of p-TsCN with lithiated imidazoles see: Dudfield, P. J.; Ekwuru, C. T.; Hamilton, K.; Osbourn, C. E.; Simpson, D. J. Synlett 1990, 277; cuprates: Westmijze, H.; Vermeer, P. Synthesis 1977 784; ketone enolates: Kahne, D.; Collum, D. B. Tetrahedron Lett. 1981, 22, 5011; and organozinc halides: Klement, I.; Lennick, K.; Tucker, C. E.; Knochel, P. Tetrahedron Lett. 1993, 34, 4623.
3. For a review on the oxidation of thioethers see: Madesclaire, M. Tetrahedron 1986, 42, 5459.
4. For 1,3-dithiolane 1-oxides and the rearrangement of these compounds see: Lee, W. S.; Lee, K.; Nam, K. D.; Kim, Y. J. Tetrahedron 1991, 47, 8091.
5. For 1,3-dithiane 1-oxides see: Page, P. G. B.; Prodger, J. C.; Westwood, D. Tetrahedron 1993, 49, 10355; Page, P. G. B.; Shuttleworth S. J.; Schilling, M. B.; Tapolczay, D. J. Tetrahedron Lett. 1993, 34, 6947; Page, P. G. B.; Allin, S. M.; Collington, E. W.; Carr, R. A. E. J. Org. Chem, 1993, 58, 6902.
6. For reviews on Lawesson's reagent see: Cherkasov, R. A.; Kutyrev, G. A.; Pudovik, A. N. Tetrahedron 1985, 41, 2567; Cava, M. P.; Levinson, M. I. Tetrahedron 1985, 41, 5061.
7. For Diels-Alder cycloadditions of thiones see: Weinreb, S. M.; Staib, R. R. Tetrahedron 1982, 38, 3087 and references cited therein, Pinto, I. L.; Buckle, D. R.; Rami, H. K.; Smith, D. G. Tetrahedron Lett. 1992, 33, 7597 and references cited therein.
8. For 3,6.dihydro-2H-thiopyran 1-oxides see: Porskamp, P. A. T. W.; van der Leij, M.; Lammerink, B. H. M.;. Zwanenburg, B. Recl. Trav. Chim. Pays-Bas 1983, 102, 400; Porskamp, P. A. T. W.; van de Wijdeven, A. M.; Zwanenburg, B. Recl. Trav. Chim. Pays-Bas 1983, 102, 506; Porskamp, P. A. T. W.; Haltiwanger, R. C.; Zwanenburg, B. Tetrahedron Lett. 1983, 24, 2035; Lenz, B. G.; Regeling, H.; Zwanenburg, B. Tetrahedron Lett. 1984, 25, 5947; van den Broek, L. A. G. M.; Porskamp, P. A. T. W.; Haltiwanger, R. C.; Zwanenburg, B. J. Org. Chem. 1984, 49, 1691; Rewinkel, J. B. M.; Zwanenburg, B. Recl. Trav. Chim. Pays-Bas 1990, 109, 190.
9. For a review on tributyltin hydride reductions see: Neumann, W. P. Synthesis 1987, 665.
10. Corey, E. J.; Suggs, J. W. Tetrahedron Lett 1975,2647.
11. McNally, J. J.; Sanfilippo, P. J.; Fitzpatrick, L.; Press, J. B. J. Heterocyclic Chem. 1992, 29, 247.
12. Sanfilippo, P. J.; McNally, J. J.; Press, J. B.; Fitzpatrick, L. J.; Urbanski, M. J.; Katz, L. B.; Giardino, E.; Falotico, R.; Salata, J.; Moore, J. B., Jr., Miller, W. J. Med. Chem. 1992,35,4425.
13. For sulphenylation see: Lipschutz, B. H.; Huff, B., Hagen, W. Tetrahedron Lett. 1988, 29, 3411.
14. Trost, B. M.; Curran, D. P. Tetrahedron Lett. 1981, 22, 1287.
15. Lee, N. H.; Muci, A. R.; Jacobsen, E. N. Tetrahedron Lett. 1991, 32, 5055.
16. Still, W. C.; Kahn, M; Mitra, A.; J. Org. Chem. 1978, 43,2923,

What is claimed is:

1. A thienopyran compound having one of the formulas I, II and III

I:

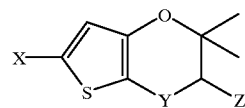

II:

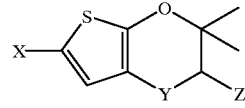

III:

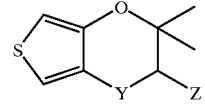

wherein
X is H or an electron-withdrawing group,
Y is an alicyclic or heterocyclic ring spiro-connected to the thienopyran ring at the position indicated by Y, the ring Y being saturated or mono-unsaturated and being substituted or unsubstituted,
Z is selected from hydrogen, hydroxy and alkoxy.

2. A thienopyran compound according to claim 1 wherein z is M.

3. A thienopyran compound according to claim 1 wherein X is an electron-withdrawing group selected from $NO_2$, CN, halogen, halogenated alkyl, alkanoyl ($C_{1-4}$), halogenated alkanoyl ($C_{1-4}$) benzoyl, acylamino ($C_{2-4}$), alkoxycarbonyl ($C_{1-4}$), CHO, COOH, COOR where R is $C_{1-4}$, CH=NOH, $CONH_2$ CON(R')$_2$ or NHCOR' where R' is alkyl ($C_{1-4}$), alkoxy ($C_{1-4}$) or phenyl, oxophosphorus and oxosulphur groups and

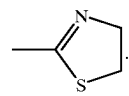

4. A thienopyran according to claim 1 wherein X is selected from CN, halogenated lower alkyl, oxophosphorus and oxosulphur groups, oxocarbon groups and —CH=NOH.

5. A thienopyran according to claim 4 wherein X is CN or —$SO_2$—Ph where Ph is substituted or unsubstituted phenyl.

6. A thienopyran according to claim 1 wherein ring Y is

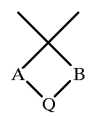

wherein Q is selected from saturated and mono-unsaturated carbon chains of 2–4 carbon atoms, and A and B fulfil one of the following: (a) both being carbon atoms, (b) one being S, SO or $SO_2$ and the other a carbon atom, (c) each being S, SO or $SO_2$, (d) one being NR" where R" is hydrogen or alkyl and the other being a carbon atom, (e) each being NR" where R" is hydrogen or alkyl; and each carbon atom of the ring Y is unsubstituted or substituted by one of alkyl, halogen or hydroxy or is a member of a carbonyl group or an epoxy ring.

7. A thienopyran compound according to claim 1 wherein Y is of the formula

wherein $S_1$ is selected from >S, >SO and >$SO_2$, $S_2$ is part of a carbon chain with Q or is selected from >S, >SO and >$SO_2$, and Q is selected from saturated and unsaturated carbon chains of 2–4 C atoms, each carbon atom of the heterocyclic ring being one of unsubstituted and substituted by one of alkyl, halogen and hydroxy, or being a member of one of a carbonyl group and an epoxy ring.

8. A thienopyran compound according to claim 7 wherein Y is selected from the following:

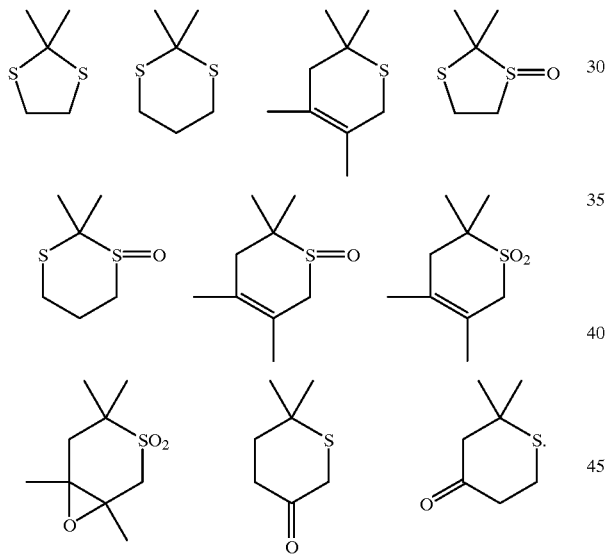

9. A thienopyran compound according to claim 8 having the formula I.

10. A pharmaceutical preparation comprising a thienopyran compound according to claim 1.

11. A composition for administration to a human or other mammal, comprising as active ingredient a thienopyran compound according to claim 1.

12. A composition according to claim 11 effective for hair growth modulation in a human or other mammal.

13. A method of modulation of hair growth in a human or other mammal, comprising topical application of a thienopyran compound according to claim 1.

14. A method of modulation of hair growth in a human or other mammal, comprising topical application of a thienopyran compound which has activity of hair growth modulation in an amount effective to provide hair growth modulation.

15. A method of modulation of hair growth in a human or other mammal, comprising topical application of an effective amount of at least one thienopyran compound having the formula I, II or III

I:

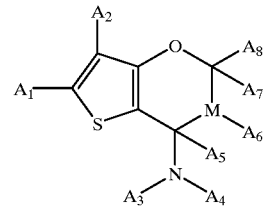

II:

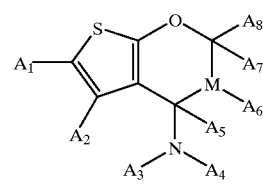

III:

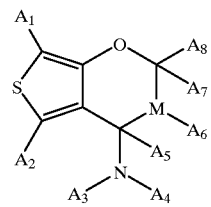

and $A_1$ and $A_2$ are selected from hydrogen, nitro, cyano, trifluoromethyl, halogen, lower alkyl ($C_{1-4}$), alkanoyl ($C_{2-4}$), substituted alkyl ($C_{1-4}$) and substituted alkanoyl ($C_{2-4}$), wherein the substituent is halogen; benzoyl, substituted benzoyl, wherein the substituent is selected from bromo, chloro, iodo, alkyl ($C_{1-4}$), alkoxy ($C_{1-4}$), acyl ($C_{2-4}$), nitro, cyano and trifluoromethyl, acylamino ($C_{2-4}$), alkoxy carbonyl ($C_{1-4}$), CHO, COOH; CH=NOH, $CONNH_2$, COOR, $CON(R)_2$ and NHCOR wherein R is alkyl ($C_{1-4}$), alkoxy ($C_{1-4}$), phenyl or substituted phenyl wherein the substituent is selected bromo, chloro, iodo, lower alkyl, lower alkoxy, nitro, cyano, trifluoromethyl and acyl ($C_{2-4}$); oxophosphorus and oxosulphur groups; and

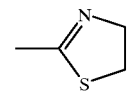

$A_3$ and $A_4$ are selected from hydrogen, hydroxy, alkanoyl ($C_{2-5}$), alkyl ($C_{1-4}$), cycloalkyl ($C_{3-6}$), cycloalkyl carbonyl ($C_{3-6}$), pyridyl carbonyl, benzoyl, substituted benzoyl wherein the substituent is selected from bromo, chloro, iodo, alkyl ($C_{1-4}$), alkoxy ($C_{1-4}$), acyl ($C_{2-4}$), nitro, cyano and trifluoromethyl, or $A_3A_4N$ together are a heterocyclic ring selected from a pyrrole, pyrrolidine or piperidine ring, a ($C_{3-9}$) lactam selected from the group consisting of isoindolone, pyrrolidinone, piperidinone, pyridinone, pyrazinone, and glycine anhydride, or substituted ($C_{3-9}$) lactam; $A_5$ is hydrogen or together with $A_6$ forms a double bond; M is CH or taken together with $A_6$ is carbonyl; $A_6$ is hydrogen, hydroxy, alkoxy ($C_{1-6}$), alkanoyloxy ($C_{2-7}$), benzoyloxy, substituted benzoyloxy; and $A_7$ and $A_8$ are hydrogen or alkyl ($C_{1-4}$) or together form a ring having 5–8 carbon atoms; and optical isomers thereof.

16. A composition for topical administration to a human or other mammal, comprising as active ingredient a thienopyran compound having one of the formulas I, II and III

I:

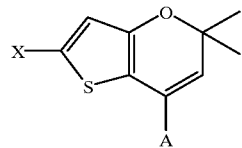

II:

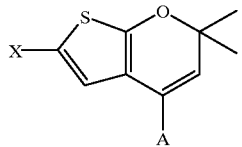

III:

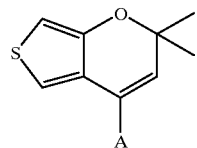

wherein
X in H or an electron-withdrawing group selected from —CN, halogenated alkyl, oxophosphorus or oxosulphur groups, oxocarbon groups, —CH=NOH and

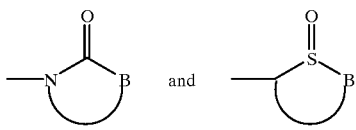

and A is one of

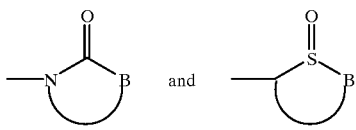

wherein B is a saturated or unsaturated carbon chain of 2–4 C atoms of which each carbon atom is unsubstituted or substituted by one of alkyl, halogen and hydroxy, or is a member of an epoxy ring, and at least one dermally acceptable formulating ingredient.

17. A composition according to claim 16, therein X is —CN.

18. A composition according to claim 16, wherein A is selected from the following:

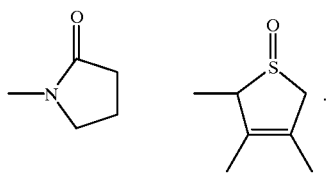

19. A composition for topical administration to a human or other mammal, comprising as active ingredient a thienopyran compound having one of the formulas I, II and III

I:

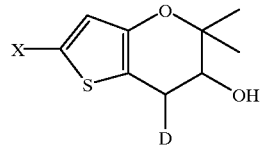

II:

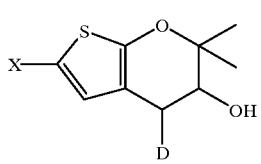

III:

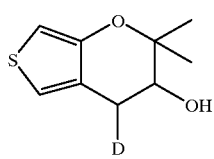

wherein
X is selected from oxophosphorus and oxosulphur groups, and
D is one of

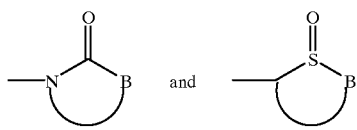

wherein B is a saturated or unsaturated carbon chain of 2–4 C atoms of which each carbon atom is unsubstituted or substituted by one of alkyl, halogen and hydroxy, or is a member of an epoxy ring, and at least one dermally acceptable formulating ingredient.

20. A composition according to claim 19, wherein X is —SO₂—Ph where Ph is substituted or unsubstituted phenyl.

21. A composition according to claim 19, wherein D is

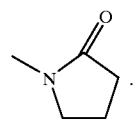

22. A method of modulation of hair growth in a human or other mammal, comprising topical application of a thienopyran compound having one of the formulas I, II and III

I:

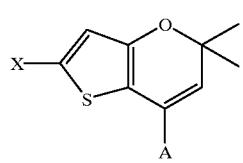

II:

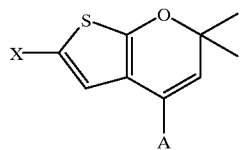

III:

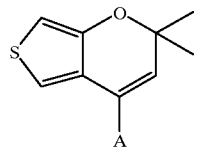

wherein

X is H or an electron-withdrawing group selected from —CN, halogenated alkyl, oxophosphorus or oxosulphur groups, oxocarbon groups, —CH=NOH and

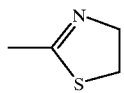

A is one of

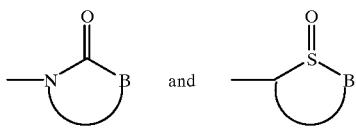

wherein B is a saturated or unsaturated carbon chain of 2–4 C atoms of which each carbon atom is unsubstituted or substituted by one of alkyl, halogen and hydroxy, or is a member of an epoxy ring, and at least one dermally acceptable formulating ingredient.

23. A method of modulation of hair growth in a human or other mammal, comprising topical application of a thienopyran compound having one of the formulas I, II and III

I:

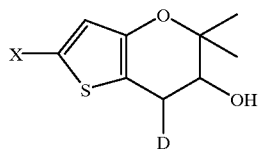

II:

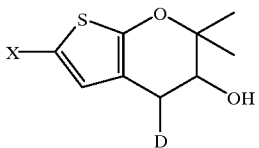

III:

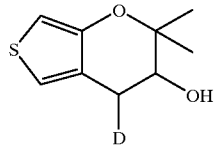

wherein

X is selected from oxophosphorus and oxosulphur groups, and

D is one of

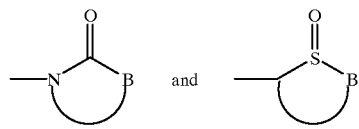

wherein B is a saturated or unsaturated carbon chain of 2–4 C atoms of which each carbon atom in unsubstituted or substituted by one of alkyl, halogen and hydroxy, or is a member of an epoxy ring, and at least one dermally acceptable formulating ingredient.

24. A composition according to claim 16 effective for hair growth modulation in a human or other mammal.

25. A composition according to claim 19 effective for hair growth modulation in a human or other mammal.

* * * * *